(12) United States Patent
Schnable et al.

(10) Patent No.: US 6,709,863 B2
(45) Date of Patent: Mar. 23, 2004

(54) NUCLEIC ACID MOLECULES ENCODING MULTIPLE START CODONS AND HISTIDINE TAGS

(75) Inventors: Patrick S. Schnable, Ames, IA (US); Feng Liu, Ames, IA (US); Yan Fu, Ames, IA (US)

(73) Assignee: Iowa State University Research Foundation, Ames, IA (US)

(*) Notice: Subject to any disclaimer, the term of this patent is extended or adjusted under 35 U.S.C. 154(b) by 0 days.

(21) Appl. No.: 09/897,776

(22) Filed: Jun. 29, 2001

(65) Prior Publication Data

US 2003/0092001 A1 May 15, 2003

Related U.S. Application Data

(63) Continuation-in-part of application No. 09/732,990, filed on Dec. 8, 2000, now Pat. No. 6,428,961.
(60) Provisional application No. 60/169,725, filed on Dec. 8, 1999.

(51) Int. Cl.[7] .............................. C12N 5/10; C12N 1/00; C12N 1/15; C12N 1/21; C12N 15/11
(52) U.S. Cl. .................... 435/325; 435/243; 435/252.3; 435/254.2; 435/320.1; 435/325; 435/419; 536/23.1; 536/24.1
(58) Field of Search ............................... 536/24.1, 23.1; 435/320.1, 325, 243, 410, 419, 252.3, 254.2

(56) References Cited

U.S. PATENT DOCUMENTS

| | | | |
|---|---|---|---|
| 4,876,197 A | 10/1989 | Burke et al. | |
| 4,880,734 A | 11/1989 | Burke et al. | |
| 5,268,284 A | * 12/1993 | Tomich et al. | 435/471 |
| 6,359,197 B1 | * 3/2002 | Amasino et al. | 800/290 |

FOREIGN PATENT DOCUMENTS

| EP | 0 120 551 B1 | 8/1990 |
|---|---|---|
| EP | 0 164 556 B1 | 3/1994 |
| EP | 0 284 044 B1 | 3/1994 |

OTHER PUBLICATIONS

Amann and Brosius, "ATG vectors for regulated high–level expression of cloned genes in *Escherichia coli*," *Gene*, 1985, 40:183–190.
Arnold, "Metal–Affinity Separations: A New Dimension in Protein Processing," *Bio/Technology*, 1991, 9:151–156.
Ausubel et al., "Preparation and Analysis of DNA," *Current Protocols in Molecular Biology*, 1995, Chapter 2, Greene Publishing and Wiley–Interscience, New York.
Ausubel et al., *Current Protocols in Molecular Biology*, 1998, John Wiley & Sons, Inc. (Table of Contents only).
Avramova et al., "Gene identification in a complex chromosomla continumm by local genomic cross–referencing," *Plant J*., 1996, 10(6):1163–1168.
Carels and Bernardi, "Two Classes of Genes in Plants," *Genetics*, 2000, 154:1819–1825.
Civardi et al., "The relationship between genetic and physical distances in the cloned *al–sh2* interval of the *Zea mays* L, genome," *Proc. Natl. Acad. Sci. USA*, 1994, 91:8268–8272.
Cohen et al., "Functional expression in yeast of the *Escherichia coli* plasmid gene coding for chloramphenicol acetyltransferase," *Proc. Natl. Acad. Sci. USA*, 1980, 77(2):1078–1082.
Cross et al., "Purification of CpG islands using a methylated DNA binding column," *Nat. Genet*., 1994, 6:236–244.
Cui et al., "The *rf2* Nuclear Restorer Gene of Male–Sterile T–Cytoplasm Maize," *Science*, 1996, 272:1334–1336.
de Boer et al., "The *tac* promoter: A functional hybrid derived from the *trp* and *lac* promoters," *Proc. Natl. Acad. Sci. USA*, 1983, 80:21–25.
de Fatima Bonaldo et al., "Normalization and Subtraction: Two Approaches to Facilitate Gen Discovery," *Genome Res*., 1996, 6:791–806.
Dellaporta et al., "Maize DNA Minpreps," *Maize Genetics Cooperation Newsletter*, 1983, 57:26–29.
Dill et al., "*Rf8* and *Rf\**Mediate Unique *T–urf13*–Transcript Accumulation, Revealing a Conserved Motif Associated With RNA Processing and Restoration of Pollen Fertility in T–Cytoplasm Maize," *Genetics*1997, 147(3):1367–1379.
Hansen et al., "The *glossy1* Locus of Maize and an Epidermis–Specific cDNA from *Kleinia odora* Define a Class of Receptor–Like Proteins Required for the Normal Accumulation of Cuticular Waxes," *Plant Physiol*., 1997, 113:1091–1100.
Henikoff et al., "Isolation of a gene from *Drosophila* by complementation in yeast," *Nature*, 1981, 289(5793):33–37.
Hollenberg, "Cloning with 2–μm DNA Vectors and the Expression of Foreign Genes in Saccharomyces cerevisiae," *Curr. Topics Microbiol. Immunol*., 1981, 96:119–144.
Hsia and Schnable, "DNA Sequence Analyses Support the Role of Interrupted Gap Repair in the Origin of Internal Deletions of the Maize Transposon, MuDR," *Genetics*, 1996, 142(2):603–618.

(List continued on next page.)

Primary Examiner—Terry McKelvey
(74) Attorney, Agent, or Firm—Fish & Richardson P.C., P.A.

(57) ABSTRACT

Compositions and methods for identifying nucleotide fragments that contain an open reading frame are provided. Compositions comprise a nucleotide sequence that encodes, in each of the three possible reading frames, an ATG start codon and a histidine tag, and vectors comprising such a nucleotide sequence. The vectors may be provided with cloning sites for insertion of nucleotide sequences of interest 5' or 3' to the 3-frame His-tag DNA sequence. Vectors also are provided with cloning sites for inserting nucleotide sequences of interest 3' of the ATG start codon and 5' of the 3-frame His-tag DNA sequence.

14 Claims, 7 Drawing Sheets

OTHER PUBLICATIONS

Lindner et al., "Specific Detection of His–Tagged Proteins with Recombinant Anti–His Tag scFv–Phosphatase or scFv–Phage Fusions," *BioTechniques*, 1997, 22:140–149.

Mercereau–Puijalon et al., "Synthesis of a chicken ovalbumin–like protein in the yeast *Saccharamyces cerevisiae*," *Gene*, 1980, 11:163–167.

Panthier et al., "Cloned β–Galactosidase Gene of *Escherichia coli* is Expressed in the Yeast *Saccharomyces cerevisiae*," *Current Genetics*, 1980, 2:109–113.

Rabinowicz et al., "Differential methylation of genes and retrotransposons facilitates shotgun sequencing of the maize genome," *Nat. Genet.*, 1999, 23:305–308.

Sambrook et al., *Molecular Cloning: A Laboratory Manual*, 1989, $2^{nd}$ Edition, Cold Spring Harbor Laboratory Press, Plainview, New York (Table of Contents only).

Shimatake and Rosenberg, "Purified γ regulatory protein cII positively activates promoters for lysogenic development," *Nature*, 1981, 292(5819):128–132.

Studier and Moffatt, "Use of Bacteriophage T7 RNA Polymerase to Direct Selective High–Level Expression of Cloned Genes," *J. Mol. Biol.*, 1986, 189:113–130.

Tijssen, *Laboratory Techniques in Biochemistry and Molecular Biology—Hybridization with Nucleic Acid Probes*, 1993, vol. 24, Chapter 2, pp. 19–78, Elsevier, New York.

Tikhonov et al., "Colinearity and its exceptions in orthologous *adh* regions of maize and sorghum," *Proc. Natl. Acad. Sci. USA*, 1999, 96(13):7409–7414.

Wagner et al., "Transcriptional slippage occurs during elongation at runs of adenine or thymine in *Escherichia coli*," *Nucleic Acids Res.*, 1990, 18(12):3529–3535.

Weigel et al., "Activation Tagging in Arabidopsis," *Plant Physiol.*, 2000, 122:1003–1013.

Wise et al., "*Mutator*–Induced Mutations of the *rf1* Nuclear Fertility Restorer of T–Cytoplasm Maize Alter the Accumulation of T–*urf13* Mitochondrial Transcripts," *Genetics*, 1996, 143:1383–1394.

Xia et al., "Cloning and Characterization of *CER2*, an Arabidopsis Gene That Affects Cuticular Wax Accumulation," *Plant Cell*, 1996, 8:1291–1304.

Xia et al., "Developmental and Hormonal Regulation of the Arabidopsis *CER2* Gene That Codes for a Nuclear–Localized Protein Required for the Normal Accumulation of Cuticular Waxes," *Plant Physiol.*, 1997, 115:925–937.

Xu et al., "Meiotic Recombination Break Points Resolve at High Rates at the 5' End of a Maize Coding Sequence," *Plant Cell*, 1995, 7:2151–2161.

Xu et al., "Sequence Analysis of the Cloned *glossy8* Gene of Maize Suggests That It May Code for a β–Ketoacyl Reductase Required for the Biosynthesis of Cuticular Waxes," *Plant Physiol.*, 1997, 115:501–510.

* cited by examiner

Figure 1. The sequence of the 3-frame His.tag and its 3-frame translation.
Location of features:
1. MCS: 283-299 (3'-> 5')
2. Fragment containing T7 promoter region from pET17b: 299-402
3. Fragment containing a 3 5'UTR of *E. coli* ompA gene from pTriplEX: 403-631
4. Backbone from pZL1: 632-4603, 1-196
5. 3-frame His.tag: 196-283 (3'-> 5')

The constructs made for 3-frame His.tag test

T7 promoter
TAATACGACTCACTATAGGGAGACCACAACGGTTTCCCTCTAGAAATAATTT

TGTTTAACTTTAAGAAGGAGATATACATATGGCATGGCATGGCCA
      Ribosome binding site         Triple-ATGs

FIG. 5A

(Method of Marcelo Bento Soares, Genome Research 6: 791-806, 1996)

US 6,709,863 B2

NUCLEIC ACID MOLECULES ENCODING MULTIPLE START CODONS AND HISTIDINE TAGS

This application is a continuation-in-part of U.S. patent application Ser. No. 09/732,990, filed on Dec. 8, 2000, now U.S. Pat. No. 6,428, 961, which claims priority to U.S. provisional patent application Ser. No. 60/169,725. filed Dec. 8, 1999.

BACKGROUND

1. Technical Field

The invention relates to methods and materials involved in identifying and isolating a nucleic acid molecule that contains an open reading frame.

2. Background Information

The genomes of higher organisms such as most crop and livestock species as well as the human genome are complex and contain greater than 90% non-genic sequences. In such cases, genes have been identified by cloning mRNA species as cDNAs into plasmid vectors to form a cDNA library. The cDNA library is then analysed for the presence of open reading frames, regions of polynucleotides that encode proteins. This technique is refered to as the EST (expressed sequence tag) approach. Although theoretically a cDNA library should represent all genes that are expressed by a cell at a given time, in practice, the library is biased for genes expressed at high levels. Those genes that are highly expressed or those that are expressed under "standard" conditions are well represented in the cellular mRNA pool, will be well represented in the cDNA library and so will be readily identified. Those genes that are expressed at low levels, however, are poorly represented in the cellular mRNA pool and may not be recovered. Furthermore, genes expressed under "unusual" conditions would not be recovered if these unusual conditions cannot be duplicated in the laboratory. In contrast to the cellular mRNA pool, all genes are represented in equi-molar concentrations in the genome. For this reason, a genomic DNA library is more advantageous than a cDNA library for gene discovery if a method can be found for differentiating clones containing genic sequences from those containing nongenic sequences.

SUMMARY

The invention involves materials and methods for identifying nucleotide fragments that contain uninterrupted open reading frames (ORFs). The materials include isolated nucleic acid molecules that encode histidine tags in each of the three possible reading frames. A histidine tag is defined as a sequence of three or more consecutive histidine amino acid residues. A DNA sequence that codes for histidine tags in all three possible reading frames is referred to as a 3-frame His-tag DNA sequence. The isolated nucleic acid molecules can be of any length, but typically are less than 500 nucleotides in length for example, less than 200, 150, or 100 nucleotides in length. In some cases, they can be greater than 500 nucleotides in length. The sequences of two representative nucleic acid molecules that encode histidine tags in each of the three reading frames are given.

The invention also includes vectors containing the above described 3-frame His-tag encoding DNA sequences. These vectors are plasmid, phage DNA or other DNA molecules that are able to replicate in a host cell. These vectors may have a selectable marker and any necessary expression control sequences. Such control sequences include, for example, promoters that allow for expression of an ORF in nucleotide sequences operably linked to these promoters.

The vectors may also have multiple cloning sites (MCS) located 3', 5', or 3' and 5' of the 3-frame His-tag coding sequence for expression of 3' or 5' histidine tagged polypeptides.

Other embodiments of the invention include cultured cells containing vectors having a 3-frame His-tag coding sequence. The cells can be prokaryotic or eukaryotic, for example, yeast cells, bacterial cells, plant cells and animal cells.

The invention can be used for determining the presence or absence of an open reading frame in any nucleic acid molecule. The nucleic acid molecule is inserted in a vector having a 3-frame His-tag coding sequence, either 3' or 5' of the 3-frame His-tag sequence. The vector is introduced into a host cell and the host cell is then cultured under conditions that allow for expression of the cloned nucleic acid molecule. The presence or absence of an open reading frame in the nucleic acid molecule of interest is then indicated by the presence or absence of a histidine tagged polypeptide encoded by the nucleic acid molecule and produced by the host cell. The advantage of this method is that if a gene exists in a nucleic acid molecule, it will be expressed with a histidine tag regardless of its reading frame in the nucleic acid molecule. Furthermore, this method allows for identification of new genes from cDNAs, ESTs, or genomic DNA. The advantage of using genomic DNA as a source for new gene discovery is the ability to recover genes that are expressed in low amounts or in conditions that may not be reproducible in the laboratory. In addition, since most genes are represented in equimolar amounts in the genome, they are more equally likely to be identified than through use of cDNA libraries derived from cellular mRNA pools.

In another embodiment, the invention allows for recovery of the corresponding polypeptide encoded by the newly identified gene without prior knowledge of the biochemical properties of the polypeptide, its activity or even characteristics of its gene sequence. Once a nucleic acid molecule is determined as encoding an ORF in the method described above, the histidine tagged ORF can be purified by affinity purification using a Ni-NTA (nickel-nitrilotriacetic acid) substrate.

In yet another embodiment, the 3-frame His-tag DNA sequence of this invention is used in activation tagging vectors. An activation tagging vector containing a 3-frame His-tag coding sequence can be introduced into an organism and allowed to randomly insert into the genome. The organism is then analysed for a change in phenotype. The gene associated with the phenotype is then isolated from other genomic DNA fragments based on its proximity to the 3-frame His-tag sequence. The function of the gene can be elucidated by analysis of the phenotype associated with the insertion event. The invention also provides for the complement of the 3-frame His-tag sequence that can be used for identification of DNA fragments containing the 3-frame His-tag sequence.

The term "nucleic acid" as used herein encompasses RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector. In addition, a non-naturally-occurring nucleic acid can include a nucleic acid molecule that is part of a hybrid or fusion nucleic acid sequence.

It will be apparent to those of skill in the art that a nucleic acid existing among hundreds to millions of other nucleic acid molecules within, for example, cDNA or genomic libraries, or gel slices containing a genomic DNA restriction digest is not to be considered an isolated nucleic acid.

The term "operably linked" as used herein, means a functional linkage between the expression control sequence and the coding sequence to which it is linked. The operable linkage permits the expression control sequence to control expression of the coding sequence. Expression control sequences can include a promoter, a transcriptional activator binding sequence, an enhancer sequence or any other regulatory or non-regulatory sequence that may be required for transcription and translation of the coding sequence to which the expression control sequence is linked.

The invention provides an isolated nucleic acid that encodes three start codons; each start codon is located within one of the three reading frames. The start codons can be ATG codons and can be found within a span of 50 nucleotides. In one embodiment, the nucleic acid encoding the three start codons has the sequence 5' ATGGCATGGCATG 3' (SEQ ID NO: 18). The isolated nucleic acid that encodes the three start codons also can have a ribosome-binding site positioned 5' of the start codons.

In another embodiment, the invention provides for a vector that has a portion that encodes three start codons, one in each reading frame. The start codons can be ATG codons that occur within a span of 13 nucleotides, and more specifically, the 13 nucleotides can have the sequence 5' ATGGCATGGCATG 3' (SEQ ID NO: 18). Furthermore, the vector that has a portion encoding three start codons also can have a portion that encodes histidine tags in three reading frames. In addition, a ribosome-binding site can be positioned 5' of the start codons. One or more cloning sites can be located 3', 5', or 3' and 5' of the portion encoding histidine tags to facilitate cloning. The vector can be, for example, the pHis6 vector.

In another embodiment, the invention provides a cultured cell having the vector that has a portion that encodes three start codons, one in each reading frame. The cell can be a prokaryotic or an eukaryotic cell. The cell can be a yeast cell, a bacterial cell, a plant cell, or an animal cell.

In another embodiment, the invention provides a method for determining the presence or absence of an open reading frame in a nucleic acid molecule among a population of nucleic acid molecules. The method involves inserting nucleic acid molecules into the vector that has a portion encoding three start codons or three histidine tags in the different reading frames, introducing the resulting vector into a host cell, culturing the host cell containing the resulting vector under conditions that allow expression of the inserted nucleic acid molecule, and determing the presence or absence of a histidine tagged polypeptide encoded by the nucleic acid molecule. The presence of a histidine tagged polypeptide indicates that the nucleic acid molecule has an open reading frame. The method can be used to identify open reading frames in genomic DNA, cDNA, EST sequences, as well as in non-genomic DNA such as inserts in artificial chromosomes. The host cell can be a prokaryotic or an eukaryotic cell, for example a plant or an animal cell. More specifically, the host cell can be a yeast or a bacterial cell.

In another embodiment, the invention provides a nucleic acid that is the complement of the isolated nucleic acid that encodes three start codons in each of the three possible reading frames.

In another embodiment, the invention provides a method for isolating a polypeptide encoded by a nucleic acid molecule. The method involves determining if the nucleic acid molecule of interest encodes an open reading frame, using the method described above, then isolating the histidine tagged polypeptide by known methods.

In another embodiment, the invention provides an isolated nucleic acid having the sequence of SEQ ID NO:15.

In another embodiment, the invention provides an isolated nucleic acid having the sequence of SEQ ID NO:16.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 5A is the sequence of part of the T7 promoter, the ribosome binding site, and the triple-ATG sequence in the ORF Rescue vector. (SEQ ID NO:17).

DETAILED DESCRIPTION

Figure 1:
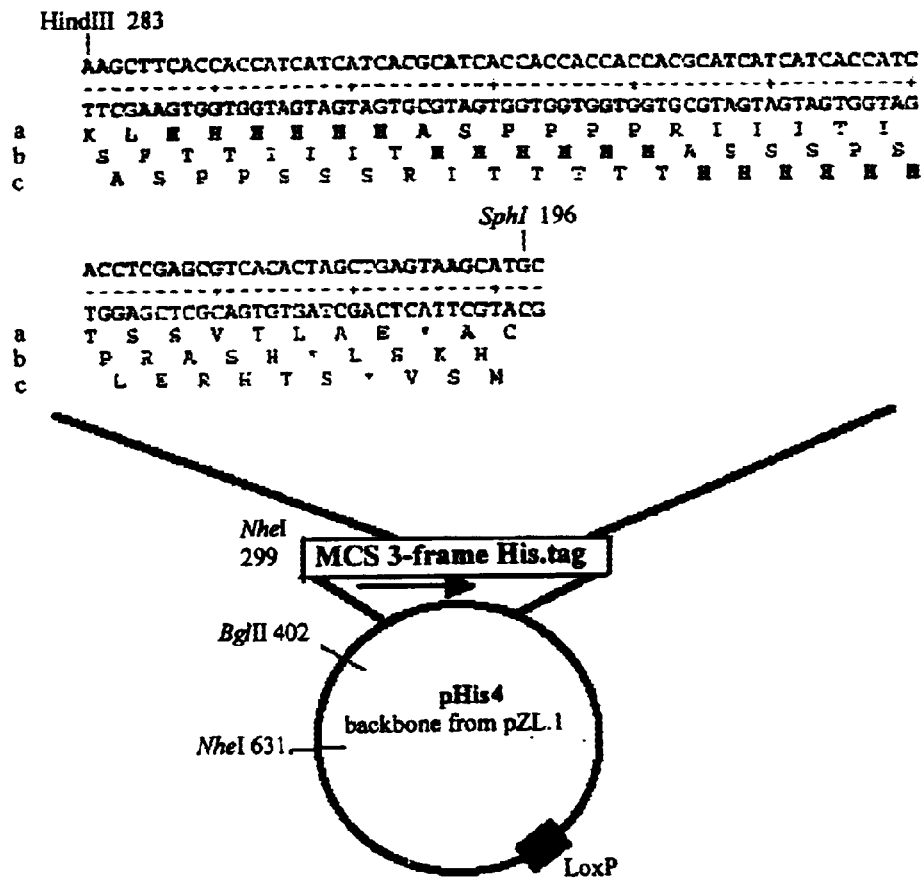
FIG. 1 is a diagrammatic illustration of the 3-frame His-tag coding sequence and its location within the structure of the pHis4 vector. The 3-frame His-tag coding region is 93 base pairs in length and spans the region of nucleotides 196 to 283 (SEQ ID NOs:1, 21, 24, and 26, where SEQ ID NO:26 is the complementary strand). The protein translation for each of the three frames is shown below the nucleic acid sequence (SEQ ID NOs:20 (frame 1), 22–23 (frame 2), and 25 (frame 3). Poly-histidine residues comprising the histidine tag of each reading frame are shown in bold. The MCS is located 5' to the frame his-tag coding sequence aat nucleic acid positions 283 to 299. The arrow indicates the direction of translation. The T7 promoter, used for expression of a protein that is cloned 3' of the MCS, is located at positions 299 to 402. Nucleotides 403–631 contain the 5' untranslated region of the *E. coli* ompA gene, obtained from the plasmid pTrip1EX, while the remaining region of the pHis4 plasmid, nucleotides 632–4603 and nucleotides 1–196, is derived from the pZL1 plasmid.

The invention relates to the use of a nucleotide sequence that encodes histidine tags in each of the three possible reading frames for identifying polynucleotide fragments that contain open reading frames.

1. 3-Frame His-Tag Coding Sequence

DNA sequences that encode histidine tags in all three reading frames are provided (SEQ ID 1 and 2). As used herein, a histidine tag is a sequence of three or more consecutive histidine amino acid residues of a polypeptide. The number of histidine residues in the tag may vary. Generally, 3 to 12 or more residues can be included. Preferably, 5 to 10 or more preferably, 6 to 8 histidine residues will be encoded in each of the three possible reading frames. The 3-frame His-tag DNA sequence can be any sequence that codes for histidines tag in each of the three possible reading frames. This 3-frame His-tag DNA sequence can have various lengths for example 500, 450, 400, 350, 300, 250, 200, 150, 100, 75, 65, 45, 35, 30, or 29 nucleotides. In some cases, it may be desirable for the 3-frame His-tag DNA sequence to be longer than 500 nucleotides and such lengths are within the scope of the present invention. For example, the 3-frame His-tag DNA sequence can be 750, 1000, 1500, 2000, 5000, 10000 or more nucleotides in length.

It is recognized that genes, in the form of DNA, are transcribed into mRNA molecules (messenger RNA) in a process referred to as transcription. The sequence of the resulting mRNA specifies a polypeptide sequence. The mRNA is read in blocks of three successive nucleotides, called codons, each codon representing an amino acid. In translation, proteins are synthesized from mRNA molecules by translating the RNA codons into the corresponding polypeptide sequence. Since a mRNA molecule is read in successive blocks of three nucleotides without omitting a nucleotide, any given mRNA molecule can be considered a sequence consisting of blocks of three nucleotides, each block having a first, second and third position. In this case, for any mRNA molecule, three different reading frames are possible depending on whether the first, second or third nucleotide of the mRNA molecule is used as the beginning of the message.

The first amino acid of a polypeptide is usually indicated on the mRNA molecule by the AUG start codon, although other start codons are known. The end of the polypeptide is indicated on the mRNA molecule in the form of an UAA, UGA or an UAG stop codon. The position of the nucleotide A in the AUG start codon and the position of the nucleotide U in any of the three stop codons determine the reading frame of the mRNA molecule. Although mRNAs are read in blocks of three nucleotides and three reading frames are possible, typically, only one of the reading frames in the mRNA sequence is the ORF of a native polypeptide.

The nucleotide sequences of the invention allow for the translation of a histidine tag regardless of the reading frame used in the gene sequence that is upstream or downstream of the 3-frame His-tag DNA sequence. That is, the triplet code is capable of encoding histidine residues in any of the three reading frames. This is illustrated in the following example. Although many sequences can code for three or more histidine residues in all three reading frames, the following sequence is illustrative.

```
                                              (SEQ ID NO:1)
5' AAG CTT CAC CAC CAT CAT CAT CAC GCA TCA CCA CCA

CCA CCA CGC ATC ATC ATC ACC ATC ACC TCG AGC GTC

ACA CTA GCT GAG TAA GCA TGC 3'
```

In the first reading frame, i.e., if the first nucleotide in this sequence is considered the first nucleotide position of a codon, the translation of this sequence will be:

```
5' AAG CTT CAC CAC CAT CAT CAT CAC GCA TCA CCA CCA
   K   L   H   H   H   H   H   H   A   S   P   P

CCA CCA CGC ATC ATC ATC ACC ATC ACC TCG AGC GTC
 P   P   R   I   I   I   T   I   T   S   S   V

ACA CTA GCT GAG TAA GCA TGC 3'   (SEQ ID NO:1)
 T   L   A   E   *   A   C       (SEQ ID NO:20)
```

In the second reading frame, i.e., if the second nucleotide in this sequence is considered the first nucleotide position of a codon, the translation of this sequence will be:

```
5' A AGC TTC ACC ACC ATC ATC ATC ACG CAT CAC CAC
    S   F   T   T   I   I   I   T   H   H   H

CAC CAC CAC GCA TCA TCA TCA CCA TCA CCT CGA GCG
H   H   H   A   S   S   S   P   S   P   R   A

TCA CAC TAG CTG AGT AAG CAT GC 3'    (SEQ ID NO:21)
S   H   *   L   S   K   H           (SEQ ID NOs:
                                     22 and 23)
```

And finally, in the third reading frame, i.e., if the third nucleotide in this sequence is considered the first nucleotide position of a codon, the translation of this sequence will be:

```
5' AA GCT TCA CCA CCA TCA TCA TCA CGC ATC ACC ACC
      A   S   P   P   S   S   S   R   I   T   T

ACC ACC ACG CAT CAT CAT CAC CAT CAC CTC GAG CGT
T   T   T   H   H   H   H   H   H   L   E   R

CAC ACT AGC TGA GTA AGC ATG C 3'    (SEQ ID NO:24)
H   T   S   *   V   S   M           (SEQ ID NO:24)
```

Since the codons specifying the amino acid histidine can be CAC or CAT as shown above, many permutations of the above sequence can code for a histidine tag in all three reading frames provided the sequence satisfies the following criteria. The 3-frame His-tag DNA sequence can be defined as having three histidine tag-coding regions and two joining regions. Each histidine tag-coding region would have at least three repetitions of the CAX codon, wherein the X can be a C or a T. Each of the three histidine tag-coding regions is separated by a joining region that has N number of nucleotides, wherein N is a number not divisible by three. The joining region can have any nucleotide sequence so long as a stop codon does not exist in the same frame and is not positioned 5' of the histidine tag-coding region. The three histidine tag-coding regions and the two joining regions form a continuous sequence referred to as the 3-frame His-tag DNA sequence. The invention provides for any sequence meeting the above description that codes for a run of at least three histidine residues in each of the three reading frames.

2. Cloning Vectors Containing the 3-Frame-His-Tag DNA Sequence

The 3-frame-His-tag DNA sequence of the invention may be used as part of a standard cloning vector. A "vector" can be a plasmid, phage DNA, or other DNA sequence that is able to enter and replicate in a host cell. The vector can also contain a marker suitable for use in identifying transformed cells. The 3-frame-His-tag DNA sequence can be used in a wide range of vectors.

In constructing the vectors of the invention, several elements are required. First, the vector must have a DNA segment containing a functional origin of replication also known as a replicon. The origin of replication allows for replication of the vector in a particular host cell. Plasmids and phage DNA by their very nature contain replicons facilitating replication in a host cell.

The vectors of the invention can be used in a wide range of host organisms, including without limitation gram-negative prokaryotic organisms such as *Escherichia coli*, Serratia, Pseudomonas; gram-positive prokaryotic organisms, such as Bacillus, Streptomyces; and eukaryotic organisms such as Saccharomyces. Additionally, host cells may include insect cells, plant cells and animal cells, for example, mammalian cells. See, for example, Sambrook et al. (1989) *Molecular Cloning: A Laboratory Manual* (2d ed., Cold Spring Harbor Laboratory Press, Plainview, N.Y.).

Expression vectors containing a 3-frame-His-tag DNA sequence preferably have at least one unique restriction site, useful for cloning a DNA sequence of interest into the vector. The cloning site can be located 3' or 5' to the 3-frame-His-tag DNA sequence. Cloning sites 5' of the 3-frame-His-tag DNA sequence can allow for expression of a polypeptide with a 3' histidine tag. Cloning sites 3' of the 3-frame-His-tag DNA sequence can allow for expression of a polypeptide with a 5' histidine tag.

Figure 5B:
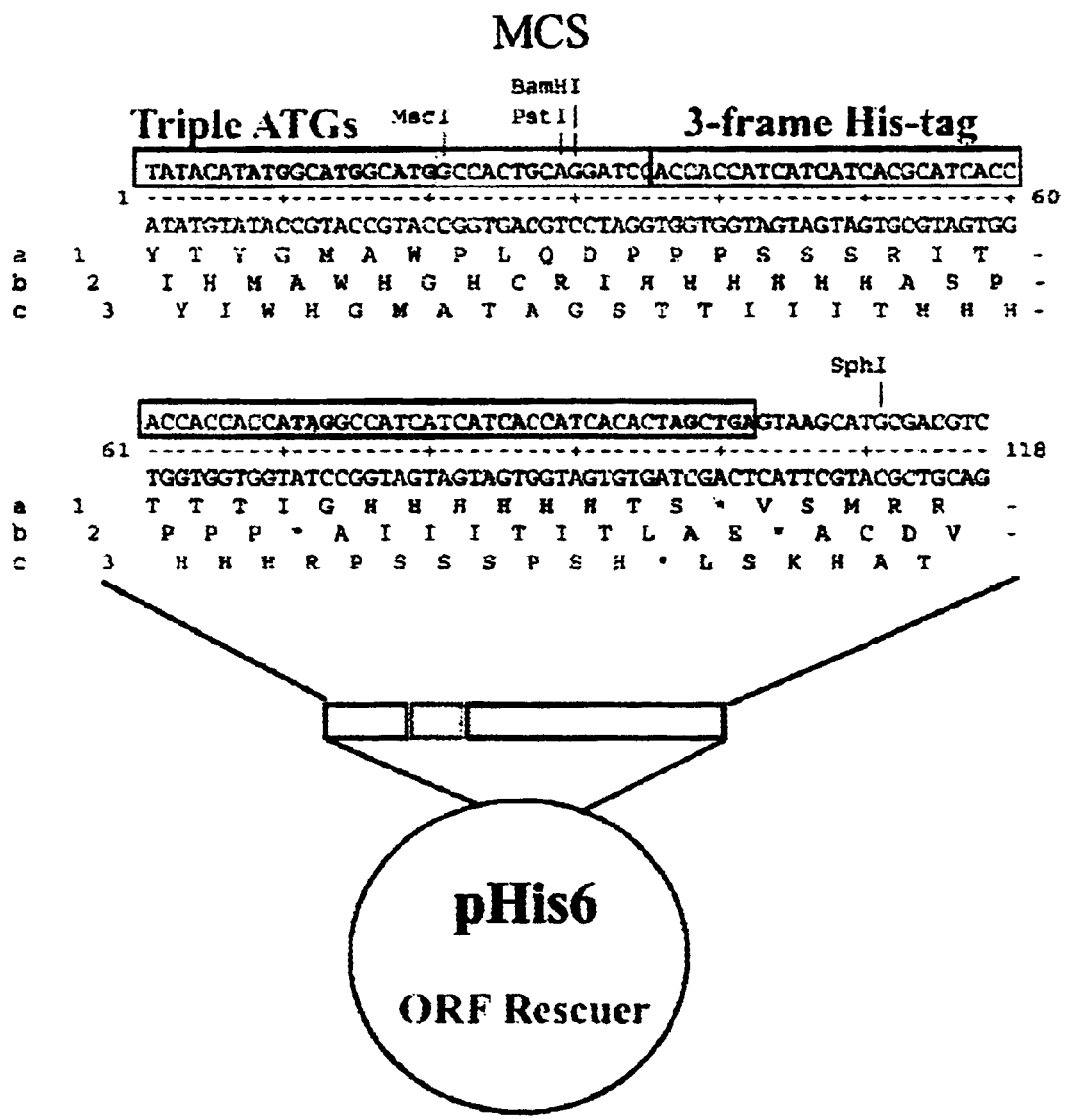
FIG. 5B is a diagrammatic illustration of the ORF Rescue vector, pHis6. The 3-frame His-tag coding region is 118 base pairs in length (SEQ ID NOs:27, 30, 34, and 37, where SEQ ID NO:37 is the complementary strand). The protein translation for each of the three frames is shown below the nuceic acid squence (SEQ ID NOs:28–29 (frame 1),31–33 (frame 2), and 35–36 (frame 3).

Although in a gene, an ORF begins with a start codon, often AUG, and ends with any of the three stop codons, the insert that is expressed in an expression vector of this invention may not have an endogenous start or stop codon. Instead, these can be provided in the vector. Vectors designed for expression of 3' or 5' histidine-tagged proteins can have one or more start codons, e.g., one in each of the three possible reading frames. A sequence that encodes three ATG start codons, one in each open reading frame, is referred to herein as a triple-ATG sequence. An example of a vector that has a triple-ATG sequence is shown in FIG. 5A. A vector can have a triple-ATG sequence located 5' of a 3-frame His-tag DNA sequence such that an insert, inserted between the triple-ATG sequence and the 3-frame His-tag DNA sequence, can be translated into a polypeptide sequence from any of the three possible open reading frames provided no stop codon is present. An example of a vector containing a triple-ATG sequence and a 3-frame His-tag DNA sequence, referred to as an ORF Rescue vector, is shown in FIG. 5B.

Typically, a multiple cloning site (MCS) is located between the triple-ATG sequence and the 3-frame His-tag DNA sequence to allow for inserting a nucleic acid fragment of interest. Nucleic acid fragments of interest can be derived from various sources, for example, genomic DNA or DNA inserted in artificial chromosomes (AC) such as bacterial artificial chromosomes and yeast artificial chromosomes. Before inserting into the ORF Rescue vector, nucleic acid fragments of interest are obtained by cleavage of larger nucleic acid molecules such as genomic DNA or DNA inserted in artificial chromosomes into useful lengths using any appropriate method. For example, nucleic acids can be fragmented by random shearing or by restriction enzyme digestion. Once inserted into the ORF Rescue vector, the three ATG start codons allow for translation from any of the three open reading frames regardless of the manner in which the nucleic acid fragment is inserted into the ORF Rescue vector.

Expression vectors may also have a ribosome-binding site (RBS). Essentially, the 3-frame His-tag DNA coding sequence and, typically, a MCS, are oriented in such a way that both the cloned DNA fragment of interest and the histidine tag encoding sequence are operably linked with expression control sequences. Expression control sequences include promoter sequences, transcriptional activator binding sequences or any sequences that are necessary for expression of the gene to which the control sequence is linked.

The insert that is used in the expression study can be any DNA molecule, for example a genomic DNA fragment, an EST generated by random or poly-T primers and a full-length or nearly full-length cDNA containing a 3' or 5' untranslated region generated by random primers or poly-T primers.

The vector may contain a gene that conveys to a transformable host cell a property useful for selection of transformed cells from non-transformed cells. Any property can be used for selection purposes, including specific nutritional conditions or antibiotic resistance, for example, tetracycline, ampicillin, apramycin, gentamycin, hygromycin or thiostrepton resistance.

The vectors of the invention may also include a promoter sequence that is capable of driving expression of a gene immediately downstream of the promoter in the host cell of interest. The promoter of choice will depend upon the host cell utilized and can be organism-specific. The promoter can be one that is active in either a prokaryotic or eukaryotic cell. The promoter also can be one whose activity is augmented or attenuated by certain growth conditions or the presence of certain chemical inducers or inhibitors. For example, the promoter can be responsive to arabinose, galactose, IPTG, or it can be a heat shock promoter.

A variety of plant and animal promoters are known, any of which may be used in the practice of the invention. For bacterial host cells, controllable transcriptional promoters may be used, for example, the lac, trp, tac promoters and the like. Promoters that regulate expression of genes in *E. coli* are known in the art. Such promoters include, but are not limited to, a bacteriophage λ pL promoter (Shimatake et al. (1981) *Nature* 292:128), a hybrid trp-lac promoter (Amann et al. (1983) *Gene* 40:183 and de Boer et al. (1983) *Proc. Natl. Acad. Sci.* 80:21), and a bacteriophage T7 promoter (Studier and Moffatt (1986) *J. Mol. Biol.* 189:113). Methods to express genes in *E. coli* using the above identified promoters are described in detail in Sambrook et al (1989) *Molecular Cloning: a Laboratory Manual* (2d ed., Cold Spring Harbor Laboratory Press, Plainview, N.Y.).

Suitable native yeast promoters include, but are not limited to, the wild-type α-factor promoter and promoters for the glycolytic enzymes phosphoglucoisomerase, phosphofructokinase, phosphotrioseisomerase, phosphoglucomutase, enolase, pyruvate kinase (PyK), glyceraldehyde-3-phosphate dehydrogenase (GAP or GAPDH), and alcohol dehydrogenase (ADH). See, for example, EPO Publication Nos. 120 551, 164 556, and 284 044.

Synthetic hybrid promoters including the upstream activator sequence of one yeast promoter, which allows for inducible expression, and the transcription activation region of another yeast promoter, also can serve as functional promoters in a yeast host. Examples of hybrid promoters include ADH/GAP, where the inducible region of the ADH promoter is combined with the activation region of the GAP promoter (U.S. Pat. Nos. 4,876,197 and 4,880,734). Other hybrid promoters using upstream activator sequences of either the ADH2, GAL4, GAL10, or PHO5 genes combined with the transcriptional activation region of a glycolytic enzyme such as GAP or PyK are available in the art (EPO Publication No. 164,556); herein incorporated by reference.

Yeast-recognized promoters also include naturally occurring non-yeast promoters that bind yeast RNA polymerase and initiate transcription of the coding sequence. Such promoters are available in the art. See, for example, Cohen et al. (1980) *Proc. Natl. Acad. Sci. USA* 77:1078; Mercereau-Puigalon et al. (1980) *Gene* 11: 163; Panthier et al. (1980) *Curr. Genet.* 2:109); Henikoff et al. (1981) *Nature* 283:835; and Hollenberg et al. (1981) *Curr. Topics Microbiol. Immunol.* 96:119; herein incorporated by reference.

The vector also may contain a translational control sequence such as an appropriately positioned RBS. It is recognized that other components or sequences may be included in the vectors of the invention.

The promoter and the 3-frame His-tag DNA sequence also may be provided in expression cassettes. Such expression cassettes are provided with a MCS for insertion of DNA fragments to be under the transcriptional regulation of the promoter.

The vector can also be used for in vitro expression studies. For example in in vitro transcription and translation, studies, cell free cell lysates can be used as the source of enzymes required for transcription and translation. Cell free lysates can be that of any cell type described above.

3. Expression of Cloned Genes

Once constructed, the vector containing the DNA sequences to be expressed is introduced into the appropriate host cell in a number of ways including for example by transformation, transfection, electrophoration and conjugation. Methods for transformation are known in the art. See, for example, Sambrook et al. (1989) *Molecular Cloning: a Laboratory Manual* 2d ed., Cold Spring Harbor Laboratory Press, Plainview, N.Y.; and Ausubel et al. (1998) *Current Protocols in Molecular Biology* (John Wiley & Sons, Inc.).

Once obtained, transformants are then grown in conditions that allow for the expression of genes encoded by the vector as well as any uninterrupted DNA sequence of interest. Conditions for gene expression depend on the promoter used in the vector but can include growth of the organism in the presence of inducer substances such as arabinose, galactose or IPTG.

4. Identification of Clones Expressing Histidine Tagged Proteins

Colonies expressing histidine tagged proteins can be identified by conventional techniques such as Western immunodetection. Colonies on a plate, for example, can be transferred to a membrane upon which cells are fixed and lysed. Any histidine tagged proteins expressed by an individual colony can be detected by in situ western colony hybridization using antibodies specific for the histidine tag or using a Ni-NTA reagent as described in the Qiaexpress Detection and Assay Handbook (Qiagen). Total proteins from a cell culture can also be prepared, separated by electrophoresis on a gel matrix such as a polyacrylamide gel, and transferred to a membrane for western detection using appropriate antibodies or Ni-NTA.

One advantage to expression of DNA sequences using a 3-frame His-tag DNA sequence is the ease of purification. The expressed recombinant protein containing the histidine tag is suitable for affinity purification on Ni-NTA agarose. One ml of Ni-NTA agarose will bind about 5 mg to 10 mg of histidine-tagged fusion protein. Methods for isolation are known in the art; see for example, Ausubel et al., supra. See also, F. H. Arnold (1991) *Biotechnology* 9:151. Any other means known in the art for the identification of histidine tagged proteins or DNA sequences may be utilized.

5. Applications of the 3-Frame-His-Tag Coding Sequence

The vectors containing a 3-frame His-tag DNA sequence, such as those described above, can be used for the identification of ORFs in a population of nucleotide molecules. For example, ORFs can be identified from genomic DNA. In this method, genomic DNA from an organism of interest is isolated. The DNA is then fragmented into useful sizes and inserted into a cloning site 3' to the promoter sequence and 5' to the 3-frame-His-tag DNA sequence. Only fragments encoding an ORF will be translated into histidine tagged proteins. Translation of any fragment that contains a stop codon would terminate at the stop codon and a histidine tagged protein would not be expressed. Histidine tagged proteins can be identified by detection of the histidine tag as described in the section above.

Useful DNA fragments can have various lengths, ranging from, for example, 100 base pairs to greater than 4 000 base pairs. Optimal insert size will vary depending of the purpose of the experiment. To maximize the probability of identifying most or all genes in the genome of an organism, a useful insert size would be smaller than the average exon size, as this would decrease the number of false negative clones. False negative clones are defined as clones that show no expression of a histidine tagged protein due to the presence of stop codons in the cloned fragment. Furthermore, the shorter the size of insert, the less likely an insert would include intronic sequences.

Using this approach, vectors containing the 3-frame his-tag DNA sequence of this invention can be used to identify and isolate new genes from the genome of any organism for which genomic DNA can be obtained.

The invention is also useful for purification of the unknown gene and corresponding polypeptide. For example, once a cell culture has been shown to produce a histidine tagged protein, the plasmid can be isolated by conventional methods and then sequenced. The newly found histidine tagged polypeptide can be purified by conventional protein purification methods such as affinity purification using Ni-NTA agarose specific for histidine tagged proteins (Ausubel et al., supra. See also, F. H. Arnold (1991) *Biotechnology* 9:151).

The invention is also useful for the expression and purification of a large collection of polypeptides. Since the 3-frame His-tag sequence allows for expression of any reading frame in the insert that is uninterrupted by a stop codon, it is possible to purify the polypeptides encoded by most of the cDNAs that are expressed by a given cell. For example, a cDNA library of expressed genes can be generated by RT-PCR using random or polyT primers. Each fragment of the cDNA library can be cloned into a vector of this invention. The 3-frame His-tag DNA sequence allows for any translation product to be histidine tagged provided that translation of the reading frame is not interrupted by a stop codon.

It is recognized that the methods of the invention may be utilized without the addition of a promoter. For example, the 3-frame His-tag sequence of the invention may be used in activation tagging. The 3-frame His-tag DNA sequence can be included in vectors used for activation tagging. Activation tagging vectors contain sequences that allow for random insertion into genomic DNA of an organism. The presence of transcriptional enhancers on these vectors stimulates expression of a gene adjacent to the region of insertion. Addition of a 3-frame His-tag DNA sequence will allow purification of the histidine tagged protein. Random insertion of the activation tagging vector can also result in inhibition of protein expression if the insertional event occurred in an ORF. The 3-frame His-tag DNA sequence can also be used for identification of the gene that had been affected by the insertion event. The DNA fragment containing the affected gene and the 3-frame His-tag DNA sequence can be identified by conventional hybridization using an oligonucleotide probe that will hybridize with the 3-frame His-tag sequence. Furthermore, using an appropriately labeled probe, the affected gene can be isolated by identifying and propagating a genomic DNA library clone that has the 3-frame His-tag DNA sequence.

The probe used can be a labeled polynucleotide molecule having a sequence complementary to the 3-frame His-tag DNA sequence or any polynucleotide molecule that will hybridize with the 3-frame His-tag DNA sequence under stringent hybridization conditions. By "stringent conditions" or "stringent hybridization conditions" are intended conditions under which a probe will hybridize to its complementary sequence to a detectably greater degree than to other sequences (e.g., at least 2-fold over background).

A nucleic acid fragment can hybridize under moderate stringency conditions or, preferably, under high stringency conditions to a complementary sequence. High stringency conditions are used to identify nucleic acids that have a high degree of homology to the probe. High stringency conditions can include the use of low ionic strength and high temperature for washing, for example, 0.015 M NaCl/0.0015 M sodium citrate (0.1×SSC); 0.1% sodium lauryl sulfate (SDS) at 50–65° C. Alternatively, a denaturing agent such as formamide can be employed during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is the use of 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2×SSC and 0.1% SDS.

Moderate stringency conditions refer to hybridization conditions used to identify nucleic acids that have a lower degree of identity to the probe than do nucleic acids identified under high stringency conditions. Moderate stringency conditions can include the use of higher ionic strength and/or lower temperatures for washing of the hybridization membrane, compared to the ionic strength and temperatures used for high stringency hybridization. For example, a wash solution comprising 0.060 M NaCl/0.0060 M sodium citrate (4×SSC) and 0.1% sodium lauryl sulfate (SDS) can be used at 50° C., with a last wash in 1×SSC, at 65° C. Alternatively, a hybridization wash in 1×SSC at 37° C. can be used.

An extensive guide to the hybridization of nucleic acids is found in Tijssen (1993) *Laboratory Techniques in Biochemistry and Molecular Biology-Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See also, Sambrook et al. (1989) *Molecular Cloning: A Laboratory Manual* (2d ed., Cold Spring Harbor Laboratory Press, Plainview, N.Y. ).

Vectors containing start codons in all three frames and a 3-frame His-tag DNA sequence can be used as an independent filter for the gene-rich fractions. For example, maize genomic DNA has a large proportion of non-coding sequences. The maize genome also contains a large amount of repetitive retrotransposon sequences that often contain open-reading frames. To enrich for genic sequences, an ORF Rescue vector can be used in combination with a normalization procedure described in de Fatima et al. (1996) *Genome Res* 6:791–806. The de Fatima et al. normalization approach can be used as a prefilter to remove retroelement-derived ORFs before cloning in the ORF Rescue vector. Unlike methylation-dependent filters that may filter out methylated genes or fail to remove retroelements and knob DNA (180 base pair sequence tandemly repeated many times), the de Fatima et al. normalization approach is methylation independent, and therefore is free from these biases of methylation-dependent filters. Furthermore, methylation-dependent filters such as digestion with Pst I also selects against genes with low GC content as the Pst I recognition sequence is GC rich. Since a significant proportion of genes in the maize genome are GC rich (see Carol et al. (2000) *Genetics* 154: 1819–1825), these may be missed in the Pst I based prefilter.

Figure 6:
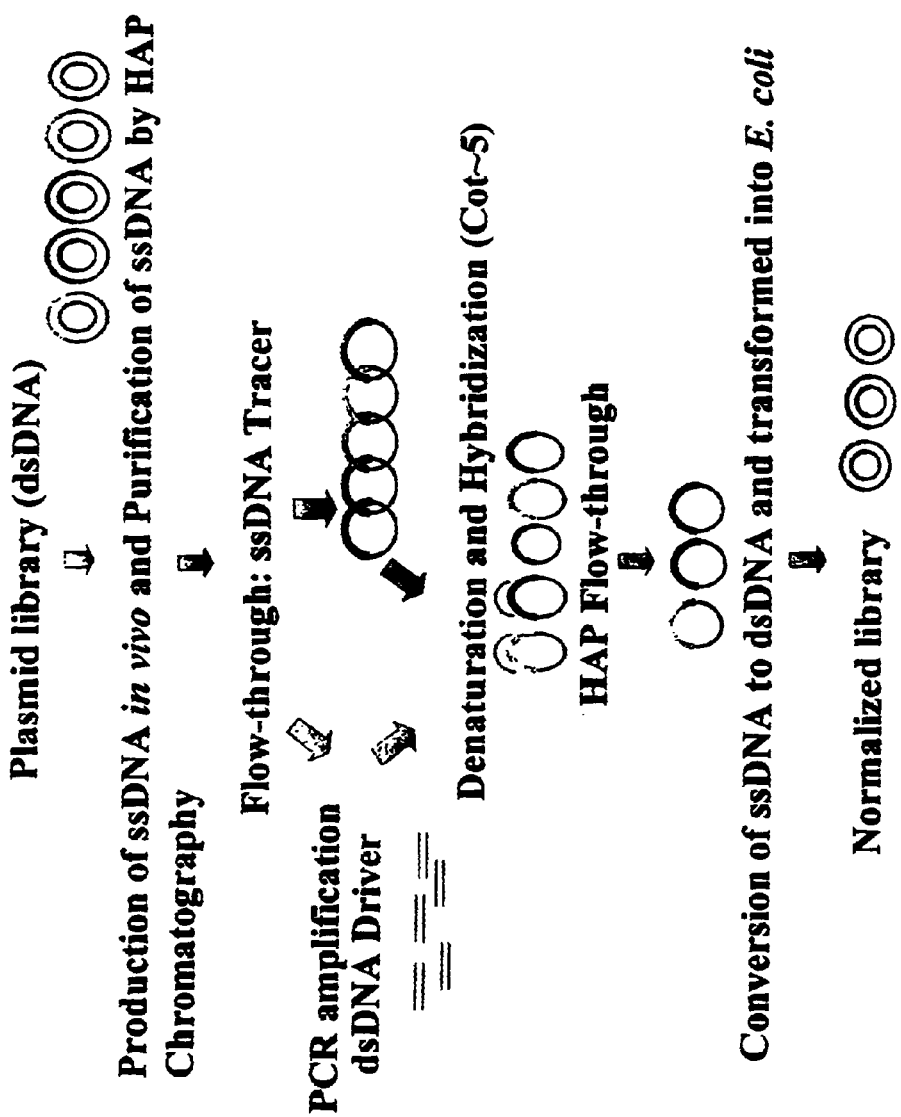
FIG. 6 is a diagrammatic illustration of the de Fatima et al. normalization procedure.

To perform the de Fatima et al. normalization procedure (see FIG. 6), maize genomic DNA is sheared to approximately 500 base pairs, polished (blunt ended), and cloned into the ORF Rescue vector. Colony hybridization using total maize DNA as probe can be used to identify clones containing repetitive retroelements. Plasmid DNA from these clones is isolated and pooled. Repetitive DNA fragments from the pooled clones are amplified using primers that flank the MCS. The resulting PCR products are denatured and used as the driver in the normalization experiment.

In parallel, several thousand additional clones from the ORF Rescue library are grown en masse in liquid culture. Plasmid DNA from this culture is denatured, or single stranded plasmid DNA can be prepared by known methods, and then allowed to reanneal with the single-stranded repetitive driver DNA. Because repetitive fragments are more likely to anneal with their complements in this procedure, the fraction that remains as single-stranded plasmid following the procedure is greatly enriched for the non-repetitive fraction of the maize genome. Double stranded repetitive retroelements can be separated from the single-stranded plasmid using hydroxyapatite chromatography. Single-stranded plasmids then can be transformed into *E. coli* cells (e.g., BL21 (DE3)), and clones containing an ORF can be identified by screening for those expressing a histidine-tagged polypeptide.

The ability of this procedure to filter out retroelement-derived ORFs can be determined via colony hybridization of the ORF Rescue library before and after normalization. If the normalization is successful in removing repetitive fragments, fewer colonies should hybridize to total maize DNA in the post-normalization library than in the pre-normalization library. The overall efficacy of this procedure can be measured by comparing the number of non-retroelement genes identified using this normalization procedure with those identified using the methylation filter alone, the methylation prefilter in combination with the ORF Rescue filter, and the ORF Rescue filter alone.

The ORF Rescue vector of the invention also can be used to identify genes on any nucleic acid molecules, for example genomic DNA from any organism as well as non-genomic DNA such as nucleic acid inserts in cosmids, yeast artificial chromosomes (YACs), or bacterial artificial chromosomes (BACs). Comparison of the ORF Rescue vector system with methylation-dependent filters (see Rabinowicz et al. (1999) *Nat Genet* 23:305–308) shows that methylation-dependent filters can only be used on genomic DNA. For example, genomic DNA cloned in BAC loses its methylation pattern after introduction into *E. coli*. Therefore, methylation-dependent filters cannot be used on nucleic acid molecules other than genomic DNA. In contrast, the ORF Rescue vector system is not methylation-dependent and can be used to filter genes from other nucleic acid types such as maize DNA cloned in BACs or YACs. Furthermore, if these ACs containing genomic DNA are characterized and positioned on physical or genetic maps, the use of the ORF Rescue vector system allows for simultaneous identification of a gene and its physical location via sequencing.

An illustrative example of the use of a BAC for simultaneous identification of a gene and its physical location is the following. Maize genomic DNA has been incorporated into 96 BACs, each BAC containing 50 to 500, or up to 1000 kilobases of maize genomic DNA. The physical map position of each BAC is known. To identify genes on BACs, DNA from each of the 96 BACs is individually sheared, polished, and cloned into 96 versions of the ORF Rescue vector. Each of the 96 versions of the ORF Rescue vector can be designed to contain a unique sequence-based "bar code" for identification. The bar code can be located 3' of the 3-frame His-tag sequence and 5' of the sequencing primer site, or 5' of the triple ATG sequence. For simplicity, the 96 ligations can then be pooled and transformed into an appropriate host. To identify ORFs, clones expressing a histidine-tagged polypeptides are selected, and the inserts are sequenced. Following sequencing, the identified gene and the map position of the clone is determined by reference to the bar code present in each of the corresponding sequence files. In this way, by sequencing a clone expressing a histidine-tagged polypeptide, a gene and its location can be determined.

A useful control for this procedure can be the identification of genes already known to reside on BACs that have already been sequenced. Examples of cloned regions that can be used include the al-sh2 interval (Civardi et al. (1994) *Proc Natl Acad Sci* 91:8268–8272) and the regions surrounding the adh1 (Tikhonov et al. (1999) *Proc Natl Acad Sci* 96:7409–14) and bz1 (unpublished data) loci.

In another embodiment, the ORF Rescue vector can be used to determine whether novel ORFs define monocot-specific genes. It is likely that some of the ORFs identified that do not exhibit sequence similarity to any known gene are novel genes. To determine whether newly discover ORFs that do not exhibit sequence similarity to known genes are novel genes, MicroArray-based hybridizations can be performed. DNA can be amplified by PCR, and then subjected to MicroArray-based hybridizations using mRNAs from a variety of organs at various stages of development. Those fragments that exhibit hybridization in any of these microarray experiments are likely to represent novel monocot-specific genes.

The invention will be further described in the following examples, which do not limit the scope of the invention described in the claims.

EXAMPLES

Example 1

Construction of 3-Frame Histidine Tag-Encoding Oligonucleotide and Expression Vectors a. 3-Frame Histidine Tag Encoding Oligonucleotides SEQ ID NO: 1 and SEQ ID NO: 2 are oligonucleotide sequences that encode a histidine tag in all three reading frames. Both 3-frame His-tag oligonucleotide molecules were synthesized by the Iowa State University Nucleic Acid Facility.

The His-tag DNA sequence 1 (SEQ ID NO:1) has HindIII and SphI sites at the 5' and 3' ends, respectively. They are used for cloning into a vector. SEQ ID NO: 1 has the following sequence:

(SEQ ID NO:1)
5' AAG CTT CAC CAC CAT CAT CAT CAC GCA TCA CCA CCA

CCA CCA CGC ATC ATC ATC ACC ATC ACC TCG AGC GTC

ACA CTA GCT GAG TAA GCA TGC 3'

For cloning into a vector, the His-tag DNA sequence 2 (SEQ ID NO:2) was synthesized with KpnI and XhoI sites at the 5' and 3' ends respectively. SEQ ID NO:2 has the following sequence:

(SEQ ID NO:2)
5' GTA CCC ACC ACC ATC ATC ATC ACG CAT CAC CAC CAC

CAC CAC GCA TCA TCA TCA CCA TCA CCT CGA 3' b. Sequences of the PCR Primers and Linkers Used in Vector Constructions

| Linker 1a: | 5' CTG CAG CGG CCG CG 3' | (SEQ ID NO:3) |
|---|---|---|
| Linker 1b: | 5' CTA GGC GCC GGC GAC GTC TCG A 3' | (SEQ ID NO:4) |
| Linker 2a: | 5' CTA GCT GCA GAT ATC A 3' | (SEQ ID NO:5) |
| Linker 2b: | 5' AGC TTG ATA TCT GCA G 3' | (SEQ ID NO:6) |
| ZL2: | 5' CCA TCG ATC CGA GAT AGG GTT GAG T 3' | (SEQ ID NO:7) |
| HT1: | 5' ACG AGC TCA GGC AGA GAC GA 3' | (SEQ ID NO:8) |
| HT2: | 5' ACG AGC TCG CAG AGA CGA CG 3' | (SEQ ID NO:9) |
| ZL1: | 5' CCT CGA GTC ACA CAG GAA ACA GCT AA 3' | (SEQ ID NO:10) |
| ZL3: | 5' GGC TAG CAG CTG TTT CCT GTG TGA 3' | (SEQ ID NO:11) |
| ZL4: | 5' GTG GAG CAT CTG GTC GCA 3' | (SEQ ID NO:12) |
| ZL8: | 5' GAG ATC TGC CAT AAC ATG TCA TCA TAG CTG TTT CCT G 3' | (SEQ ID NO:13) |
| ZL10: | 5' GAG ATC TGC CAT AAC ATG TCA TCA TAG CTG TTT CCT G 3' | (SEQ ID NO:14) |
| T7 Linker: | 5'1 CTA GCC GAA ATT AAT ACG ACT CAC TAT AGG GAG AC 3' | (SEQ ID NO:15) |
| pHis6L: | 5' TAT ACA TAT GGC ATG GCA TGG CCA CTG CAG GAT CCA CCA CCA TCA TCA TCA CGC ATC ACC ACC ACC 3' | (SEQ ID NO:16) | c. The Triple-ATG Sequence and Upstream Region (SEQ ID NO: 17)
5' TAATACGACTCACTATAGGGAGACCACAACGGTTTCCCTCTAGAAAT
AATTTTGTTTAACTTTAAGAAGGAGATATACATATGGCATGGCATGGCCA
3'

(SEQ ID NO. 18)
5' ATGGCATGGCATG 3'.

d. Construction of Cloning Vectors pHis4, pHis5, and pHis6

Plasmid pZL1 was excised in vivo by infecting E. coli Y1090 cells with λZIPLOX phage (GIBCO-BRL Cat #15397-029). The following modifications were made in pZL1 (see FIG. 1). The His-tag DNA sequence (SEQ ID NO: 1) of FIG. 1 was inserted into the 3' end of a multiple cloning site (MCS). The promoter region was replaced with a T7 promoter fragment from pET17b (Novagen). A linker was formed using two oligonucleotides (Linker 1a and 1b). The oligonucleotides have the sequences 5' CTG CAG CGG CCG CG 3' and 3' AGC TCT GCA GCG GCC GCG GAT C 5' (SEQ ID NO: 3 and 4, respectively). The linker was used to replace the fragment between the SacI and BamHI sites. In the same step, a PstI site was introduced and a XbaI site was removed. To facilitate translation from each of the reading frames, a triple-reading frame translation cassette containing a slippage site (see Wagner et al. (1990) *Nucleic Acids Res* 18:3529–3535), obtained from pTrip1EX (Clontech), was inserted 5' of the MCS. This pTrip1EX fragment also contained the 5' UTR of the E. coli ompA gene and a LAC promoter. The slippage site was removed by digestion with Kpn I and Nhe I when experiments showed that it did not facilitate translation, but an NheI-BglII fragment containing the 5' UTR of the E. coli ompA gene and the LAC promoter remained in the vector. The modified vector, named pHis4, is shown in FIG. 1.

Figure 2:
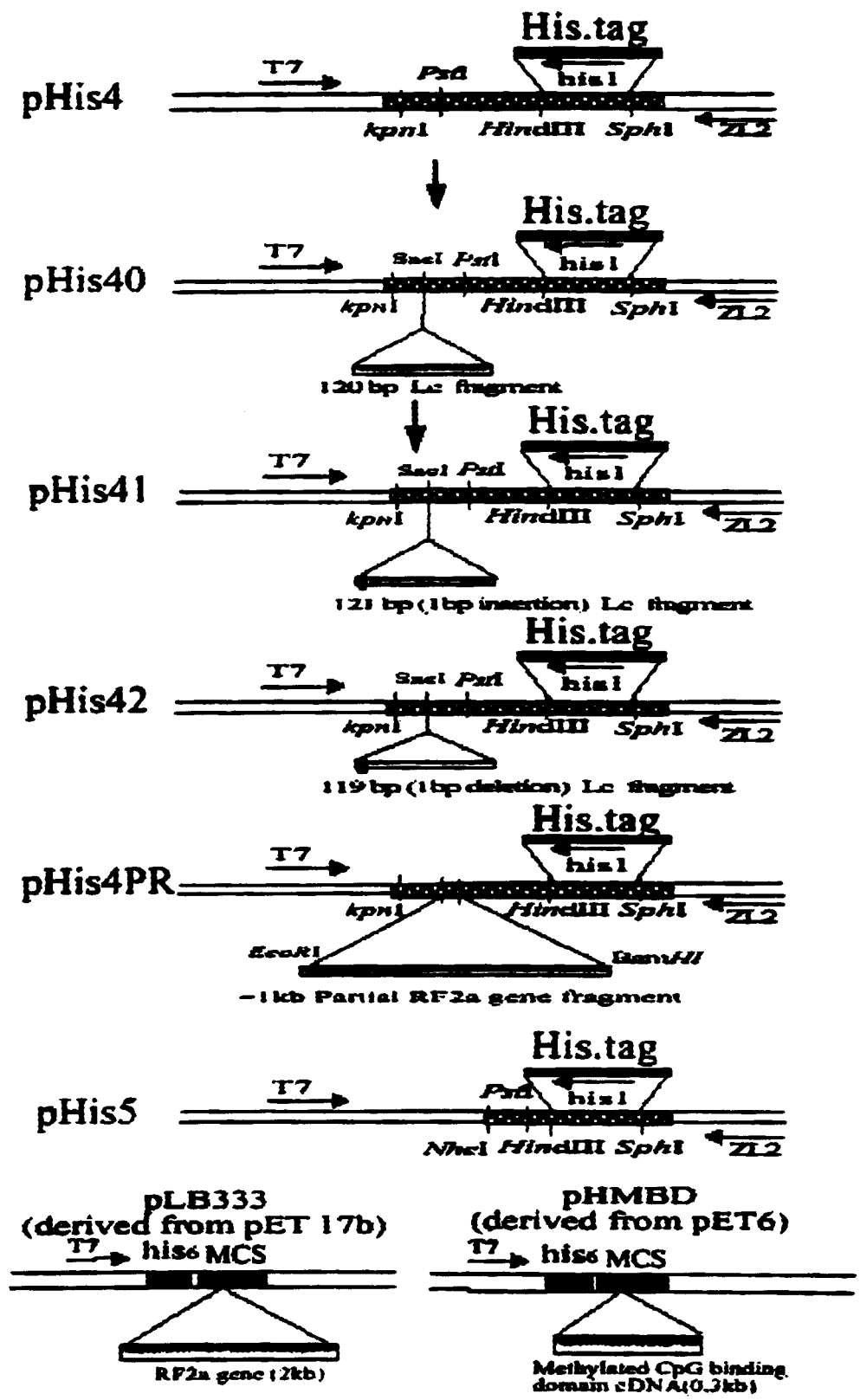
FIG. 2 is a summary of the constructs derived from the pHis4 vector used in the expression studies. The histidine tag-coding region is labeled as His-tag. The pHis40 plasmid contains a 120 base pair fragment of the Lc gene 5' of the histidine tag coding region. The pHis41 plasmid has the same insert fragment as pHis40 with an additional nucleotide while the insert in pHis42 has the same insert fragment as pHis40 with a nucleotide deletion. The plasmids pHis40, pHis41 and pHis42 represent the three possible reading frames of the 120 base pair fragment of the Lc gene. The plasmid pHis4PR contains an one kilobase gene encoding a partial RF2a protein. Location of the T7 promoter is indicated. Additional plasmids used in the study include pLB333, which has a rf2a gene, and pHMBD, which contains a gene for methylated CpG binding domain.

The plasmid pHis4 expresses a small polypeptide of 62 amino acids that is encoded by the MCS. For this reason, the empty pHis4 vector sometimes yields a false positive result when in situ or regular western analysis is performed. However, polypeptides less than 30 amino acids in length can be easily degraded in vivo (Qiaexpress Detection and Assay Handbook). To shorten the 62 amino acid polypeptide encoded by pHis4, the MCS fragment of pHis4 was shortened in the following way. A pair of oligonucleotides (Linker 2a and 2b) having the sequence 5'-CTA GCT GCA GAT ATC A-3' and 3'-GAC GTC TAT AGT TCG A-5' (SEQ ID NO: 5 and 6) was synthesized by the Iowa State University Nucleic Acid Facility. These were annealed to form a double-stranded linker having NheI and HindIII cohesive termini. This double stranded linker was then ligated into pHis4 digested with NheI and HindIII and the resulting pHis5 plasmid was generated. Plasmid pHis5 is shown in FIG. 2.

The effectiveness of this modification in reducing the incidence of false positive clones was demonstrated by the finding that the small polypeptide was not detected in either regular or in situ western analysis using the immunochemical method with anti-his antibody (Qiaexpress Detection and Assay Handbook).

To generate pHis6, two oligonucleotides, pHis6L and pHis6R, were used. The oligonucleotides, synthesized with Nde I and Sph I sites, were annealed, and the resulting dimer was digested with the restriction enzymes Nde I and Sph I. The digested oligonucleotide dimer was ligated into a pHis5 vector that also had been digested with Nde I and Sph I. The resulting vector was named pHis6. Vector pHis6 is also referred to as the ORF Rescue vector. FIG. 5A shows the sequences of part of the T7 promoter, the ribosome-binding site (RBS), and the Triple-ATG.

The vector pHis6, shown in FIG. 5B, differs from pHis5 in three aspects. First, the multiple-cloning site (MCS) in pHis5 has been replaced by a different MCS illustrated in FIG. 5. Second, pHis6 has three ATG start codons, one in each of the three open reading frames from which translation can be initiated. The presence of three ATG start codons in each of the three reading frames allows for translation of any insert containing an open reading frame. Third, the vector pHis6 also has a modified 3-frame His-tag DNA sequence located 3' of the MCS. In the absence of an insert, pHis6 expresses polypeptides less than 30 amino acids in length. Since polypeptides less than 30 amino acids in length are easily degraded in vivo, the incidence of false positive clones is reduced when pHis6 vector is used.

e. Construction of pHis41, pHis42, pHis4PR

A 120 base pair SacI fragment, part of a maize Lc cDNA gene (Genbank accession#: M26227) that had been cloned in PHP11179 (Pioneer Hi-bred International, Inc), was obtained by digesting PHP11179 with SacI. This 120 base pair SacI fragment was then inserted into pHis4. The resulting construct, pHis40, now encodes a partial Lc polypeptide.

A PCR step was performed using the template pHis40 and the primers ZL2 and HT1 (SEQ ID NO: 7 and 8 respectively). An Lc fragment containing a 1 base pair insertion was generated. The resulting Lc fragment was digested with the enzymes SacI and PstI and then directionally cloned into pHis4 to generate pHis41 (FIG. 2).

In an analogous manner, the primers ZL2 and HT2 (SEQ ID NO: 7 and 9 respectively) and the template pHis40 were used to generate PCR products containing a 1 base pair deletion. The resulting Lc fragment with a 1 base pair deletion was digested with the enzymes SacI and PstI and then directionally cloned into pHis4 to generate pHis42 (FIG. 2).

To test the expression of genes cloned in the pHis4 vector, the plasmid pHis4PR, which has a partial rf2a cDNA gene (Genbank Accession#: U43082) and therefore encodes a partial RF2A polypeptide was constructed. The strategy was as follows. The plasmid pLB333 (F. Liu et al., 2000. Mitochondrial aldehyde dehydrogenase activity is required for male fertility in maize (*Zea mays* L.) Submitted to Plant Cell.) which has the full length rf2a cDNA was digested with the restriction enzymes EcoRI and BamHI. One product of the digestion was a 2-kb EcoRI-BamHI fragment of the rf2a gene. This partial rf2a gene was then inserted 5' of the 3-frame His-tag coding region of pHis4. A 0.8-kb ApaI-ApaI fragment containing stop codons, which could prevent translation through the His-tag region, was removed. Table 1 shows the length of ORFs encoded by all constructs.

f. Construction of pSlip7

The plasmid pZL1 was obtained from in vivo excision of re-ligated EcoRI digested phage λZiplox (purchased from GIBCO-BRL, Cat #15397-029). The His-tag DNA sequence (SEQ ID NO: 2) was ligated into KpnI/XhoI digested pWF1 (plasmid pTriplEx containing an insertion at the EcoRI site) to generate pHS.

The MCS from pZL1 was PCR amplified using the ZL1 and ZL2 primers (SEQ ID NO: 10 and 7). The resulting fragment was digested with XhoI and HindIII, and ligated into XhoI/HindIII digested pHS, thereby generating pHSC.

A NheI/ApaI fragment from pZL1 was obtained by PCR amplification using the primers ZL3 and ZL4 (SEQ ID NO: 11 and 12). The resulting PCR product was digested with NheI and ApaI and then used in a three-way ligation with NheI/HindIII digested pHSC and ApaI/HindIII digested pZL1 to generate pSlip1. Plasmid pSlip1 was then digested with PstI and XhoI, treated with Mung Bean nuclease to remove single stranded termini and then re-ligated to generate pSlip2. Plasmid pSlip2 differs from pSlip1 in that a stop codon after the ATG start codon in pSlip1 no longer exists in pSlip2.

A fragment from pZL1 was PCR amplified using the primers ZL4 and ZL8 (SEQ ID NO: 12 and 13). The primers ZL4 and ZL8 were designed with a NheI site or a BglII site at the 5' end, respectively. The PCR product was digested with NheI and BglII, and then ligated into the pSlip2 vector that had been digested with NheI and BglII. The resulting vector is pSlip3. A fragment was obtained from pSlip3 by PCR using the primers ZL10 and ZL2 (SEQ ID NO: 13 and 7). The resulting PCR product was digested with BglII and HindIII, then ligated back into BglII/HindIII-digested pSlip3 to generate pSlip4.

Plasmid pSlip4 was digested with MunI and NheI. A T7 linker composed of these oligonucleotide sequences: 5' CTA GCC GAA ATT AAT ACG ACT CAC TAT AGG GAG AC 3' (SEQ ID NO:14) and 3' GG CTT TAA TTA TGC TGA GTG ATA TCC CTC TGT TAA 5' (SEQ ID NO:19), were synthesized. The linker, engineered such that the 5' terminus of each of the two strands either has a MunI or a NheI 5' cohesive overhang, was ligated with the MunI/NheI-digested pSlip4 vector to generate the pSlip7 vector.

Example 2

Western Analysis for Expression of Histidine Tagged Proteins a. IPTG Induction of Protein Expression and Western Hybridization Analysis A plasmid encoding a gene to be expressed was transformed into the *E. coli* strain BL21(DE3) for expression. Transformants were picked, inoculated in 2 ml dyt medium

TABLE 1

The length of ORFs encoded by all constructs.

|  | His-tag | phis4PR | pHis4 | pHis40 | pHis41 | pHis42 | pHis5 |
|---|---|---|---|---|---|---|---|
| The length of ORF in base pairs (bp) | 81 bp | 1020 bp | 186 bp | 303 bp | 300 bp | 291 bp | 99 bp |
| Length of encoded polypeptide in amino acids | (27 aa) | (340 aa) | (62 aa) | (101 aa) | (100 aa) | (97 aa) | (33 aa) | containing 100 μg/ml ampicillin (Sambrook et al. (1989) Molecular Cloning: A Laboratory Manual. 2d ed., Cold Spring Harbor Laboratory Press, Plainview, N.Y.) and allowed to grow overnight at 37° C. The overnight culture was then diluted 1:60 into 3 ml of fresh dyt medium and incubated with shaking until the $OD_{600}$ reached 0.6. Protein expression was induced using 1 mM IPTG for 4 hours. The 3 ml culture was then harvested by centrifugation at 4000 g and the resulting cell pellet was resuspended in 300 μl of 10 mM Tris-HCl buffer at pH 8. Proteins from 30 μl samples were mixed with an equal volume of SDS buffer and heated at 90° C. for 5 minutes. Samples were then subjected to SDS-PAGE analysis. Separated proteins were transferred to a nitrocellulose membrane using a semi-dry eletrophoretic transfer cell (Bio-Rad, Hercules, Calif.) at 20 volts for 3 hours. Immunoblot analysis with Ni-NTA or anti-his antibody was performed according to the Qiaexpress Detection and Assay Handbook (Qiagen).

b. Determination of Protein Expression from pHis4

Since RF2A antibody is available, pHis4PR, which encodes a partial RF2A protein, was used to show that histidine tagged proteins could be expressed from the pHis4 plasmid. The plasmid pLB333, which encodes a full-length RF2A protein, was used as a positive control for RF2A detection. Another plasmid, pHMBD (Cross, S H., et al. 1994. Purification of CpG islands using a methylated DNA binding column. Nat. Genet. 6: 236–244), which encodes a 6-histidine tag as well as a methylated CpG binding domain, was also used as a positive control. Since Ni-NTA forms a conjugate with the 6-histidine tag, western analysis using Ni-NTA showed that a histidine tagged protein was present in cells carrying pLB333 as well as from cells carrying the pHis4PR plasmid. The protein that reacted with Ni-NTA in the pLB333 sample was larger than that seen in the pHis4PR sample suggesting that the protein observed in the pHis4PR sample was that of a partial RF2A protein. Western analysis using antibodies specific for RF2A also showed that cultures containing the pHis4PR plasmid expressed a smaller RF2A protein compared to the full-length protein detected in cultures harboring the pLB333 positive control. Furthermore, no RF2A specific signal was detected in cultures carrying the pHMBD plasmid. These results demonstrated that genes could be efficiently translated into histidine tagged proteins when cloned in pHis4 and that these histidine tagged proteins could be specifically detected using Ni-NTA.

c. Expression of 3' Histidine Tagged Proteins from All Three Reading Frames

The plasmid constructs pHis40, pHis41 and pHis42 were used to show that a histidine tagged protein could be expressed from pHis4 regardless of the open reading frame of the cloned insert. When protein samples from cultures containing pHis40, pHis41 or pHis42 were examined by Ni-NTA Western analysis, histidine tagged proteins were detected in all three samples. This indicated that the 3-frame His-tag DNA sequence can be used to monitor translation from any of the three possible open reading frames present in a fragment cloned 5' of the 3-frame His-tag DNA sequence. Furthermore, it was found that the strongest expression was achieved with pHis40 which expressed the maize gene's native ORF. The other two clones expressed histidine tagged ORFs that are not expressed in maize and are considered non-organismal proteins (see below).

d. Expression of 5' Histidine Tagged Proteins from All Three Reading Frames

Expression from pSlip7 was studied using various rf2 gene fragments. Fragments of the rf2 gene were inserted into this vector in such a way that each of the resulting plasmids pST21, pST22 and pST23 represents one of the three possible reading frames. Expression was tested by Western blot hybridization using anti-RF2 antibodies. All three frames were expressed, although expression from one frame was slightly reduced compared to the other two.

Example 3

Determination of a Useful Size for DNA Inserts Used in Expression Studies

In order to determine the size of random maize genomic fragments that would be useful for expression from vectors containing the 3-frame His-tag DNA sequence, a simulation experiment was performed. Previously known Zea mays genes were used in the simulation study. Genomic sequences of 141 genes were used to generate random fragments of 20, 40, 60 . . . up to 1200 base pairs for the simulation experiment. For each fragment size, 400,000 random fragments were chosen for analysis. For each fragment, three predicted polypeptides, one for each of the three possible reading frames, were determined. Each predicted polypeptide sequence was then classified into three categories. A predicted polypeptide sequence is a biologically insignificant protein, referred to as a non-organismal translation product, if it is not naturally expressed in the cell from which its gene is originally obtained. The predicted polypeptide sequence can be a polypeptide that does not have a histidine tag due to the presence of a stop codon or it can be a correctly translated polypeptide, for example, a polypeptide that can be found in the organism from which the corresponding gene was originally cloned.

Figure 3:
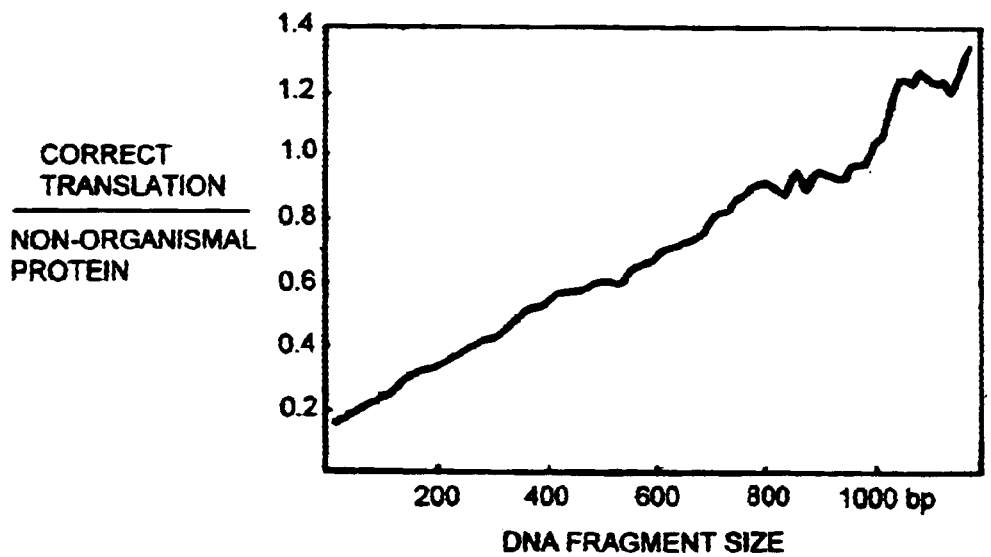
FIG. 3 is a graph illustrating the results of a simulation study demonstrating the relationship between fragment length and the ratio of correctly translated protein products to non-organismal protein products.

The results indicated that DNA fragments which are <100 base pairs in length are less than optimal for identification of true ORFs since they are too readily translated into non-organismal protein products. In contrast, a large proportion of DNA fragments, which are larger than 100 base pairs in length, is not translated due to the presence of stop codons. FIG. 3 shows the ratio of correctly translated products to non-organismal protein products observed at different fragment sizes. As the fragment length increases, the proportion of correctly translated product relative to non-organismal product increases. The jaggedness at the right end of the curve in FIG. 3 can be explained by the preponderance of "no translation" events in the sampling. The ratio of "good" (correct translation) to "bad" (non-organismal protein) simply rises and this trend will continue as chunk size increases until the ratio becomes undefined by way of all chunks of DNA failing to translate. These results demonstrate that sheared DNA fragments 100 to 1000 base pairs in length are useful for identifying biologically relevant ORFs among random genomic DNA inserts.

Example 4

Detection of Open Reading Frames in Maize Genomic DNA Fragments a Preparation of Genomic DNA Inserts Genomic DNA from immature, unpollinated maize ears was isolated using the Dellaporta method as described in Dellaporta, S L., J. Wood and J. B. Hicks, 1983; Maize DNA minpreps. Maize Genet. Coop. Newslet. 57: 26–29. DNA was then fragmented in 3 different ways: by digestion with PstI (GIBCO-BRL); by shearing with a Nebulizer (Invitrogen) at 15–20 psi (tested by gauge first) for 3 min; or by digestion with McrBC (Bio-Rad). McrBC treated and sheared DNA fragments were then subjected to Mung bean nuclease (Promega) digestion to remove single stranded termini. DNA fragments of different sizes were separated by electrophoresis on a 2% preparative agarose gel at low voltage (1–2V/cm). Four gel fractions corresponding to DNA fragments of 100–200 base pairs, 200–400 base pairs, 400–800 base pairs, and >800 base pairs were collected and the DNA was purified from the agarose gel matrix using a Qiagen gel extraction kit. Purified DNA was dissolved in 50 µl H$_2$O.

b. Vector Preparation

Vectors pHis5 and pHis4 were digested with PstI and dephosphorylated with CIAP (Promega) according to the Promega Technique Guide. For blunt-end ligations, pHis4 was digested with SmaI and then dephosphorylated. The restriction digest mixture was then separated by gel electrophoresis. DNA was purified from the gel matrix using the Qiagen gel extraction kit and dissolved in 50 µl of water.

c. Ligation and Transformation

Figure 4:
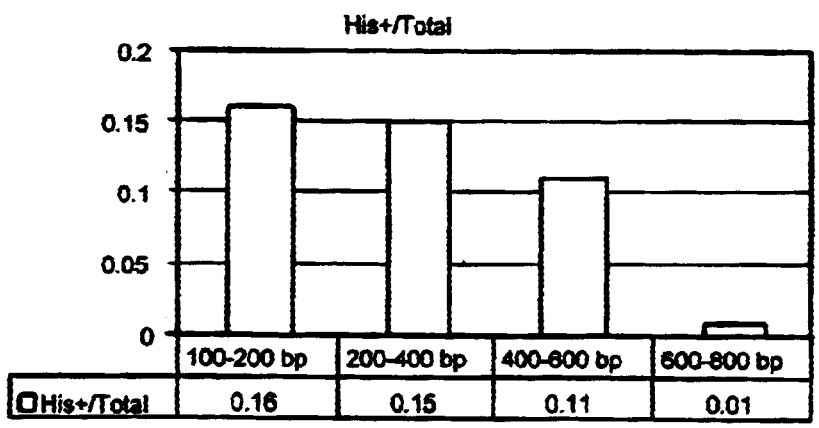
FIG. 4 is a comparison of the ratios of colonies producing histidine-tagged polypeptides to all colonies screened at different insert sizes.

Ligations were performed at an insert to vector molar ratio of 4–5:1. T4 ligase (5U/ul, GIBCO) was used at an amount of 3 µl in a 15 µl reaction volume. Reactions were performed in a thermocyler programmed for 100 cycles, each cycle consisting of incubation at 25° C. for 20 seconds followed by incubation at 16° C. for 5 minute. The ligation reactions were transformed into *E. coli* BL21(DE3) and HMS174(DE3) cells by electroporation using Gene Pulse (Bio-Rad). The resulting cultures were regenerated in 1 ml of dyt for 1 hour and then 50 µl samples were plated to check the density of the cells. The clones with BL21(DE3) as host cells and McrBC digested fragments as inserts were termed MB clones. The clones with BL21(DE3) as host cells and sheared fragments as inserts were termed SB clones. The clones with HMS174 (DE3) as host cells and sheared fragments as inserts were termed SH clones.

d. Detection of Histidine Tagged Proteins by in Situ Colony Western Hybridization Transformants were plated for isolated colonies. In situ colony western hybridization (Qiaexpress Detection and Assay Handbook, Qiagen) was used to detect colonies that expressed a histidine tagged protein. FIG. 4 summarizes the ratio of clones that expressed histidine tagged proteins to the total number of colonies that were counted at different insert sizes.

e. High-Throughput Plasmid Isolation, Sequencing and Sequence Analysis

Clones that expressed histidine tagged proteins were further analysed by plasmid isolation and sequencing. Each clone was inoculated into 1 ml dyt medium in a 96-well culture block and cultured for approximately 16 hours. Plasmid DNA from each clone was isolated using a Qiagen Biorobot System and sequenced by the Iowa State University Nucleic Acid Facility.

Sequencher 3.1 (Gene Codes Cooperation, MI) was used for searching redundancy. Batch BlastX and BlastN were used for gene annotation. Other online tools for coding sequence determination include Genseqer (http://www.zmdb.iastate.edu) and Sequence Manipulation Suite (http://www.bioinformatics.org/sms). Microsoft Excel was used for statistical analysis of large scale sequences.

f. Rescue of Maize Genomic ORFs Using pHis4 and pHis5

PstI-digested, sheared and McrBC-treated maize genomic fragments were inserted into pHis4 and pHis5 cloning vectors and then transformed into *E. coli* BL21(DE3) or HMS174(DE3) cells. After in situ colony western analysis, 173 colonies expressing histidine tagged proteins were selected for further analysis. The corresponding plasmid DNA in these colonies was extracted and sequenced. Of the 173 positive clones, 165 clones (95%) were found to contain an uninterrupted ORF. Only 4.6% (8/173) of the total number of clones had sequences that contain stop codons that would prevent translation of the histidine tag. These clones all have a start codon downstream of the stop codon for re-initiation of translation and translation through to the histidine tag. Hence, these data demonstrate that the pHis4 and pHis5 vectors can efficiently rescue ORFs directly from the maize genome.

To assign functions to the rescued sequences, these sequences were first analyzed using the batch Blast program and other online tools. The blast search results obtained for the 165 His+ clones are summarized in Table 2. Of the 165 His+ clones, 77 contained known ORFs as determined by BlastX analysis against a non-redundant protein database or tBlastX against an EST database. Of the remaining 88 clones that did not show any BlastX hits, 26 showed similarity at the nucleotide level to known genes in a nonredundant database or in an EST database, see Table 3. The remaining 62 clones that contain sequences that do not match any known genes in the databases, may code for novel genes. These results demonstrate that these vectors are powerful tools to isolate genes from a complex genome such as that of maize.

TABLE 2

The BlastX and tBlastX search results of His+ clones

BlastX (against NR) or tBlastX (against EST): Cutoff: E < 1e–5

| | |
|---|---|
| PstI-cuts: 77/186 (46%) Host cell: BL21(DE3) | Of the 55 hits: 5 are known maize proteins, e.g. lipoxygenase, actin depolymerizing factor, basic leucine zipper protein, calcium-dependent protein kinase and NADP-malic enzyme; 58 are Arabidopsis proteins, e.g. 25 known, 12 hypothetical, 8 unknown and 13 putative proteins; 14 are known proteins from other plants, e.g. 2 from *Pisum sativum*, 6 from rice, 2 from *Hordeum vulgare*, 1 from kidney bean, and 1 from Petunia, 1 from Rattus, and 1 from spinach. |
| MB clones: 9/33 (27%) Inserts: polished McrBC treated genomic DNA Host cell: BL21(DE3) | Nine clones have hits against a protein database: 3 clones match the same kind of rice retrofit retrotransposon polyprotein that is known to co-transcribe with the rice Xa21D gene; 4 clones have the same hit with a copia-type polyprotein and further analysis showed both of these retroelements have hits in a maize EST database suggesting they are active at the transcriptional level and might be hypomethylated; 2 hits are known plant proteins. |

TABLE 2-continued

The BlastX and tBlastX search results of His+ clones

BlastX (against NR) or tBlastX (against EST): Cutoff: E < 1e−5

SB 12/12 100%  All hits are retroelement polyprotein.
Inserts: polished
sheared genomic
DNA
Host cell:
BL21(DE3)
SH 1/2 (50%)  The hit is an Arabidopsis protein.
Inserts: polished
sheared genomic
DNA
Host cell:
HYF(DE3)

TABLE 3

BlastN search results of clones without BlastX hits

BlastN (against NR and EST) Cutoff: E < 1e−10

PstI-cuts: 22/109  All hits are ESTs:
  15 from maize;
  4 from rice;
  3 from sorghum cDNA libraries.
MB clones: 15/24  Fifteen clones have hits against the EST and NT databases:
  6 clones match maize ESTs;
  2 match the retroelements in the EST database;
  3 clones are rDNA;
  6 clones are repeated sequences.
SH clones: 0/1  No hit g. Rescue of Maize Genomic ORFs Using pHis6

Maize genomic DNA was sheared and polished (i.e. no prefilter) or subjected to a hypomethylation prefilter by digestion with PstI or McrBC. Since PstI does not digest methylated DNA, small PstI fragments should be derived from the hypomethylated fraction of the maize genome. McrBC digests methylated DNA at $Pu^mC[N_{40-2000}]Pu^mC$, so fragments that survive McrBC digestion should be derived from the hypomethylated fraction of the genome. The resulting fragments were ligated into ORF Rescue vectors and transformed into E. coli strain BL21 (DE3). Clones that expressed a histidine tagged polypeptide were selected and the inserts were sequenced and compared to sequences present in GenBank. The results, presented in Table 4, established that the selection schemes were effective at enriching for the gene-rich portions of the maize genome.

TABLE 4

Effect of Hypomethylation Prefilter on Rate of Gene Discovery using ORF Rescue Vector.

| Hypomethylation Prefilter | # ORFs with Match to Genes in GenBank/Total | # Genie ORFs derived from Retroelements |
|---|---|---|
| PstI Digestion | 96/186 | 0/96 |
| McrBC Digestion | 18/24 | 9/18 |
| None | 12/12 | 12/12 |

In a similar experiment, maize genomic DNA was subjected to three different hypomethylation prefilter steps: (1) digestion with PstI, (2) digestion with Sau3A1, or (3) digestion with Sau3A1 and McrBC. The resulting fragments were ligated into ORF Rescue vectors and transformed into E. coli strain BL21 (DE3) or HMS174 (DE3). Table 5 summarizes the total number of clones analyzed and the percentages of those that expressed a histidine-tagged polypeptide (% His+).

TABLE 5

ORF Rescue with methylation filters

| Genomic fragments | | % His+ | # of total clones | Host Cell |
|---|---|---|---|---|
| PstI-digested | 0.2–0.4 kb | 8.8% | 2016 | BL21(DE3) |
| | 0.4–0.8 kb | 3.8% | 1506 | |
| Sau3A1-digested | 0.2–0.4 kb | 3.9% | 1344 | BL21(DE3) |
| | 0.4–0.8 kb | 2.9% | 1152 | |
| Sau3A1-digested | 0.2–0.4 kb | 5.6% | 480 | HMS174(DE3) |
| | 0.4–0.8 kb | 4.9% | 288 | |
| Sau3A1/McrBC-digested | 0.2–0.4 kb | 8.9% | 950 | BL21(DE3) |

HMS174(DE3) expresses McrBC: recognition site $Pu^mC(N_{40-2000})Pu^mC$

Figure 7:
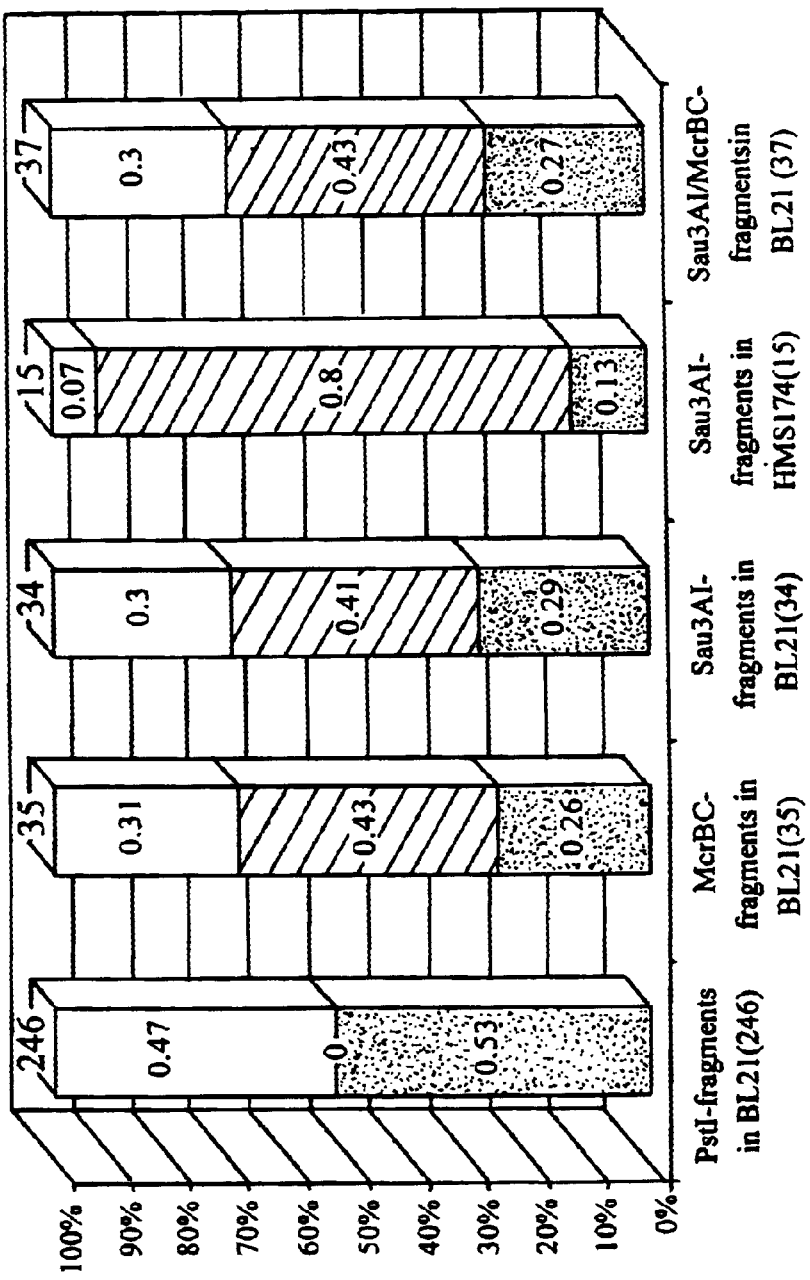
FIG. 7 is a comparison of the proportions of the 367 His+ clones having ORFs that (1) match with known genes (i.e. gene hits), (2) match with repetitive sequences, and (3) are novel ORFs.

In another similar experiment, maize genomic DNA was fragmented by enzymatic digestion with (1) Pst I, (2) McrBc, (3) Sau3AI, or (4) Sau3AI/McrBC. The resulting fragments were ligated into the ORF Rescue vector and then transformed into E. coli BL21 (DE3), or HMS174. Clones expressing histidine-tagged polypeptides were identified, sequenced, and compared to sequences present in GenBank. Results showed that 384 clones were His+, and of these, 367 (95.6%) contained ORFs. Only 4.4% of His+ clones had in-frame stop codons. It is likely that clones containing in-frame stop codons produced a histidine-tagged polypeptide through translation reinitiation. That is, the maize insert sequences likely functioned as promoters or translational reinitiation sequences in the *E. coli* host. FIG. 7 is a comparison of the proportions of the 367 His+ clones having ORFs that (1) match with known genes (i.e. gene hits), (2) match with repetitive sequences, and (3) are novel ORFs. Table 6 summarizes examples of four clones identified using the ORF Rescue vector that match with known genes in Genbank.

TABLE 6

Examples of protein hits

| Clone ID | BlastX hits | E-value |
|---|---|---|
| 0103A51 | gb|AAF73373.1|AF193835_1 LRK1 protein [*Oryza sativa*] | 4.00E−26 |

TABLE 6-continued

Examples of protein hits

| Clone ID | BlastX hits | E-value |
|---|---|---|
| 0003A60 | pir||T51329 DNA binding protein RAV1 [validated]-[Arab] | 1.00E−22 |
| 0011B23 | gb|AAB80681.1| (AC002332) putative cinnamoyl-CoA reductase [Arab] | 1.00E−08 |
| 0010A02 | gb|AAC42248.1| (AC005395) TINY-like AP2 domain transcription factor [Arab] | 7.00E−15 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid, wherein said nucleic acid comprises: three start codons within a span of 50 nucleotides, wherein each said start codon is within a different reading frame; and a sequence that encodes histidine tags in three reading frames.

2. The nucleic acid of claim 1, wherein said start codons are ATG codons.

3. The nucleic acid of claim 1, wherein said start codons are within a span of 13 nucleotides.

4. The nucleic acid of claim 3, wherein said 13 nucleotides are ATGGCATGGCATG (SEQ ID NO:18).

5. The nucleic acid of claim 1, wherein said isolated nucleic acid further comprises a ribosome-binding site positioned 5' of said start codons.

6. A vector comprising the nucleic acid of claim 1.

7. The vector of claim 6, wherein said start codons are ATG codons.

8. The vector of claim 6, wherein said start codons are within a span of 13 nucleotides.

9. The vector of claim 6, wherein said 13 nucleotides are ATGGCATGGCATG (SEQ ID NO:18).

10. The vector of claim 6, further comprising one or more cloning sites, said one or more cloning sites located 3', 5', or 3' and 5' of said sequence encoding said histidine tags.

11. A cultured cell comprising the vector of claim 6.

12. The cultured cell of claim 11, wherein said cell is a prokaryotic or eukaryotic cell.

13. The cultured cell of claim 12, wherein said cell is selected from the group consisting of a yeast cell, a bacterial cell, a plant cell and an animal cell.

14. The complement of the nucleic acid of claim 1.

* * * * *

UNITED STATES PATENT AND TRADEMARK OFFICE
CERTIFICATE OF CORRECTION

PATENT NO. : 6,709,863 B2
DATED : March 23, 2004
INVENTOR(S) : Feng Liu, Yan Fu and Patrick S. Schnable It is certified that error appears in the above-identified patent and that said Letters Patent is hereby corrected as shown below:

Title page,
Item [75], Inventors, "Feng Liu", please delete "US" and insert -- China -- therefor;
"Yan Fu", please delete "US" and insert -- China -- therefor;
Item [73], Assignee, after "Foundation" please insert -- , Inc -- therefor;
Item [56], References Cited, OTHER PUBLICATIONS, "Avramova et al." reference, please delete "chromosomla continumm" and insert -- chromosomal continuum -- therefor;
"Civardi et al." reference, after "*Zea mays L*" please delete "," and insert -- . -- therefor;
"de Fatima Bonaldo et al." reference, please delete "Gen" and insert -- Gene -- therefor;
"Hansen et al." reference, please delete "glossyl" and insert -- glossy1 -- therefor;
"Mercereau-Puijalon et al." reference, please delete "Saccharamyces" and insert -- Saccharomyces -- therefor;
"Shimatake and Rosenberg" reference, please delete "γ" and insert -- λ -- therefore.

Signed and Sealed this

Twenty-first Day of December, 2004

JON W. DUDAS
*Director of the United States Patent and Trademark Office*

SEQUENCE LISTING

```
<160> NUMBER OF SEQ ID NOS: 37

<210> SEQ ID NO 1
<211> LENGTH: 93
<212> TYPE: DNA
<213> ORGANISM: Artificial Sequence
<220> FEATURE:
<223> OTHER INFORMATION: Synthetically generated oligonucleotide
<221> NAME/KEY: CDS
<222> LOCATION: (1)...(84)
<221> NAME/KEY: CDS
<222> LOCATION: (88)...(93)

<400> SEQUENCE: 1 aag ctt cac cac cat cat cat cac gca tca cca cca cca cca cgc atc      48
Lys Leu His His His His His His Ala Ser Pro Pro Pro Pro Arg Ile
  1               5                  10                  15 atc atc acc atc acc tcg agc gtc aca cta gct gag taa gca tgc          93
Ile Ile Thr Ile Thr Ser Ser Val Thr Leu Ala Glu     Ala Cys
             20                  25                  30

<210> SEQ ID NO 2
<211> LENGTH: 66
<212> TYPE: DNA
<213> ORGANISM: Artificial Sequence
<220> FEATURE:
<223> OTHER INFORMATION: Synthetically generated oligonucleotide

<400> SEQUENCE: 2
gtacccacca ccatcatcat cacgcatcac caccaccacc acgcatcatc atcaccatca     60
cctcga                                                               66

<210> SEQ ID NO 3
<211> LENGTH: 14
<212> TYPE: DNA
<213> ORGANISM: Artificial Sequence
<220> FEATURE:
<223> OTHER INFORMATION: linker
```

-continued

```
<400> SEQUENCE: 3
ctgcagcggc cgcg                                                         14

<210> SEQ ID NO 4
<211> LENGTH: 22
<212> TYPE: DNA
<213> ORGANISM: Artificial Sequence
<220> FEATURE:
<223> OTHER INFORMATION: linker

<400> SEQUENCE: 4
ctaggcgccg gcgacgtctc ga                                                22

<210> SEQ ID NO 5
<211> LENGTH: 16
<212> TYPE: DNA
<213> ORGANISM: Artificial Sequence
<220> FEATURE:
<223> OTHER INFORMATION: linker

<400> SEQUENCE: 5
ctagctgcag atatca                                                       16

<210> SEQ ID NO 6
<211> LENGTH: 16
<212> TYPE: DNA
<213> ORGANISM: Artificial Sequence
<220> FEATURE:
<223> OTHER INFORMATION: linker

<400> SEQUENCE: 6
agcttgatat ctgcag                                                       16

<210> SEQ ID NO 7
<211> LENGTH: 25
<212> TYPE: DNA
<213> ORGANISM: Artificial Sequence
<220> FEATURE:
<223> OTHER INFORMATION: primer for PCR

<400> SEQUENCE: 7
ccatcgatcc gagatagggt tgagt                                             25

<210> SEQ ID NO 8
<211> LENGTH: 20
<212> TYPE: DNA
<213> ORGANISM: Artificial Sequence
<220> FEATURE:
<223> OTHER INFORMATION: primer for PCR

<400> SEQUENCE: 8
acgagctcag gcagagacga                                                   20

<210> SEQ ID NO 9
<211> LENGTH: 20
<212> TYPE: DNA
<213> ORGANISM: Artificial Sequence
<220> FEATURE:
<223> OTHER INFORMATION: primer for PCR

<400> SEQUENCE: 9
acgagctcgc agagacgacg                                                   20

<210> SEQ ID NO 10
<211> LENGTH: 26
```

```
<212> TYPE: DNA
<213> ORGANISM: Artificial Sequence
<220> FEATURE:
<223> OTHER INFORMATION: primer for PCR

<400> SEQUENCE: 10
cctcgagtca cacaggaaac agctaa                                          26

<210> SEQ ID NO 11
<211> LENGTH: 24
<212> TYPE: DNA
<213> ORGANISM: Artificial Sequence
<220> FEATURE:
<223> OTHER INFORMATION: primer for PCR

<400> SEQUENCE: 11
ggctagcagc tgtttcctgt gtga                                            24

<210> SEQ ID NO 12
<211> LENGTH: 18
<212> TYPE: DNA
<213> ORGANISM: Artificial Sequence
<220> FEATURE:
<223> OTHER INFORMATION: primer for PCR

<400> SEQUENCE: 12
gtggagcatc tggtcgca                                                   18

<210> SEQ ID NO 13
<211> LENGTH: 37
<212> TYPE: DNA
<213> ORGANISM: Artificial Sequence
<220> FEATURE:
<223> OTHER INFORMATION: primer for PCR

<400> SEQUENCE: 13
gagatctgcc ataacatgtc atcatagctg tttcctg                              37

<210> SEQ ID NO 14
<211> LENGTH: 35
<212> TYPE: DNA
<213> ORGANISM: Artificial Sequence
<220> FEATURE:
<223> OTHER INFORMATION: linker

<400> SEQUENCE: 14
ctagccgaaa ttaatacgac tcactatagg gagac                                35

<210> SEQ ID NO 15
<211> LENGTH: 66
<212> TYPE: DNA
<213> ORGANISM: Artificial Sequence
<220> FEATURE:
<223> OTHER INFORMATION: Synthetically generated oligonucleotide

<400> SEQUENCE: 15
tatacatatg gcatggcatg gccactgcag gatccaccac catcatcatc acgcatcacc     60
accacc                                                                66

<210> SEQ ID NO 16
<211> LENGTH: 67
<212> TYPE: DNA
<213> ORGANISM: Artificial Sequence
<220> FEATURE:
<223> OTHER INFORMATION: Synthetically generated oligonucleotide
```

<400> SEQUENCE: 16
gacgtcgcat gcttactcag ctagtgtgat ggtgatgatg atggcctatg gtggtggtgg    60
tgatgcg                                                              67

<210> SEQ ID NO 17
<211> LENGTH: 97
<212> TYPE: DNA
<213> ORGANISM: Artificial Sequence
<220> FEATURE:
<223> OTHER INFORMATION: Synthetically generated oligonucleotide

<400> SEQUENCE: 17
taatacgact cactataggg agaccacaac ggtttccctc tagaaataat tttgtttaac    60
tttaagaagg agatatacat atggcatggc atggcca                             97

<210> SEQ ID NO 18
<211> LENGTH: 13
<212> TYPE: DNA
<213> ORGANISM: Artificial Sequence
<220> FEATURE:
<223> OTHER INFORMATION: Synthetically generated oligonucleotide

<400> SEQUENCE: 18
atggcatggc atg                                                       13

<210> SEQ ID NO 19
<211> LENGTH: 35
<212> TYPE: DNA
<213> ORGANISM: Artificial Sequence
<220> FEATURE:
<223> OTHER INFORMATION: linker

<400> SEQUENCE: 19
aattgtctcc ctatagtgag tcgtattaat ttcgg                               35

<210> SEQ ID NO 20
<211> LENGTH: 28
<212> TYPE: PRT
<213> ORGANISM: Artificial Sequence
<220> FEATURE:
<223> OTHER INFORMATION: Synthetically generated peptide

<400> SEQUENCE: 20

Lys Leu His His His His His His Ala Ser Pro Pro Pro Arg Ile
  1               5                  10                  15

Ile Ile Thr Ile Thr Ser Ser Val Thr Leu Ala Glu
            20                  25

<210> SEQ ID NO 21
<211> LENGTH: 93
<212> TYPE: DNA
<213> ORGANISM: Artificial Sequence
<220> FEATURE:
<223> OTHER INFORMATION: Synthetically generated oligonucleotide
<221> NAME/KEY: CDS
<222> LOCATION: (2)...(76)
<221> NAME/KEY: CDS
<222> LOCATION: (80)...(91)

<400> SEQUENCE: 21 a agc ttc acc acc atc atc atc acg cat cac cac cac cac cac gca tca   49
  Ser Phe Thr Thr Ile Ile Ile Thr His His His His His His Ala Ser
   1               5                  10                  15 tca tca cca tca cct cga gcg tca cac tag ctg agt aag cat               91

```
Ser Ser Pro Ser Pro Arg Ala Ser His     Leu Ser Lys His
            20                  25 gc                                                                      93

<210> SEQ ID NO 22
<211> LENGTH: 25
<212> TYPE: PRT
<213> ORGANISM: Artificial Sequence
<220> FEATURE:
<223> OTHER INFORMATION: Synthetically generated peptide

<400> SEQUENCE: 22

Ser Phe Thr Thr Ile Ile Ile Thr His His His His His Ala Ser
 1               5                  10                  15

Ser Ser Pro Ser Pro Arg Ala Ser His
            20                  25

<210> SEQ ID NO 23
<211> LENGTH: 4
<212> TYPE: PRT
<213> ORGANISM: Artificial Sequence
<220> FEATURE:
<223> OTHER INFORMATION: Synthetically generated peptide

<400> SEQUENCE: 23

Leu Ser Lys His
 1

<210> SEQ ID NO 24
<211> LENGTH: 93
<212> TYPE: DNA
<213> ORGANISM: Artificial Sequence
<220> FEATURE:
<223> OTHER INFORMATION: Synthetically generated oligonucleotide
<221> NAME/KEY: CDS
<222> LOCATION: (3)...(80)
<221> NAME/KEY: CDS
<222> LOCATION: (84)...(92)

<400> SEQUENCE: 24 aa gct tca cca cca tca tca tca cgc atc acc acc acc acc acg cat       47
   Ala Ser Pro Pro Ser Ser Ser Arg Ile Thr Thr Thr Thr Thr His
    1               5                  10                  15 cat cat cac cat cac ctc gag cgt cac act agc tga gta agc atg          92
His His His His His Leu Glu Arg His Thr Ser     Val Ser Met
            20                  25 c                                                                       93

<210> SEQ ID NO 25
<211> LENGTH: 26
<212> TYPE: PRT
<213> ORGANISM: Artificial Sequence
<220> FEATURE:
<223> OTHER INFORMATION: Synthetically generated peptide

<400> SEQUENCE: 25

Ala Ser Pro Pro Ser Ser Ser Arg Ile Thr Thr Thr Thr Thr His His
 1               5                  10                  15

His His His Leu Glu Arg His Thr Ser
            20                  25

<210> SEQ ID NO 26
<211> LENGTH: 93
<212> TYPE: DNA
<213> ORGANISM: Artificial Sequence
```

```
<220> FEATURE:
<223> OTHER INFORMATION: Synthetically generated oligonucleotide

<400> SEQUENCE: 26
gcatgcttac tcagctagtg tgacgctcga ggtgatggtg atgatgatgc gtggtggtgg      60
tggtgatgcg tgatgatgat ggtggtgaag ctt                                   93

<210> SEQ ID NO 27
<211> LENGTH: 118
<212> TYPE: DNA
<213> ORGANISM: Artificial Sequence
<220> FEATURE:
<223> OTHER INFORMATION: Synthetically generated oligonucleotide
<221> NAME/KEY: CDS
<222> LOCATION: (1)...(99)
<221> NAME/KEY: CDS
<222> LOCATION: (103)...(117)

<400> SEQUENCE: 27 tat aca tat ggc atg gca tgg cca ctg cag gat cca cca cca tca tca      48
Tyr Thr Tyr Gly Met Ala Trp Pro Leu Gln Asp Pro Pro Pro Ser Ser
 1               5                  10                  15 tca cgc atc acc acc acc acc ata ggc cat cat cat cac cat cac act      96
Ser Arg Ile Thr Thr Thr Thr Ile Gly His His His His His His Thr
            20                  25                  30 agc tga gta agc atg cga cgt c                                        118
Ser     Val Ser Met Arg Arg
            35

<210> SEQ ID NO 28
<211> LENGTH: 33
<212> TYPE: PRT
<213> ORGANISM: Artificial Sequence
<220> FEATURE:
<223> OTHER INFORMATION: Synthetically generated peptide

<400> SEQUENCE: 28

Tyr Thr Tyr Gly Met Ala Trp Pro Leu Gln Asp Pro Pro Pro Ser Ser
 1               5                  10                  15

Ser Arg Ile Thr Thr Thr Thr Ile Gly His His His His His His Thr
            20                  25                  30

Ser

<210> SEQ ID NO 29
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 29

Val Ser Met Arg Arg
 1               5

<210> SEQ ID NO 30
<211> LENGTH: 118
<212> TYPE: DNA
<213> ORGANISM: Artificial Sequence
<220> FEATURE:
<223> OTHER INFORMATION: Synthetically generated oligonucleotide
<221> NAME/KEY: CDS
<222> LOCATION: (2)...(70)
<221> NAME/KEY: CDS
<222> LOCATION: (74)...(103)
<221> NAME/KEY: CDS
<222> LOCATION: (107)...(118)
```

<400> SEQUENCE: 30

```
t ata cat atg gca tgg cat ggc cac tgc agg atc cac cac cat cat cat        49
  Ile His Met Ala Trp His Gly His Cys Arg Ile His His His His His
  1               5                  10                 15 cac gca tca cca cca cca cca tag gcc atc atc atc acc atc aca cta         97
His Ala Ser Pro Pro Pro Pro     Ala Ile Ile Ile Thr Ile Thr Leu
                20                   25                 30 gct gag taa gca tgc gac gtc                                             118
Ala Glu     Ala Cys Asp Val
                35
```

<210> SEQ ID NO 31
<211> LENGTH: 23
<212> TYPE: PRT
<213> ORGANISM: Artificial Sequence
<220> FEATURE:
<223> OTHER INFORMATION: Synthetically generated peptide

<400> SEQUENCE: 31

```
Ile His Met Ala Trp His Gly His Cys Arg Ile His His His His
1               5                  10                 15

His Ala Ser Pro Pro Pro Pro
                20
```

<210> SEQ ID NO 32
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 32

```
Ala Ile Ile Ile Thr Ile Thr Leu Ala Glu
1               5                  10
```

<210> SEQ ID NO 33
<211> LENGTH: 4
<212> TYPE: PRT
<213> ORGANISM: Artificial Sequence
<220> FEATURE:
<223> OTHER INFORMATION: Synthetically generated peptide

<400> SEQUENCE: 33

Ala Cys Asp Val

<210> SEQ ID NO 34
<211> LENGTH: 118
<212> TYPE: DNA
<213> ORGANISM: Artificial Sequence
<220> FEATURE:
<223> OTHER INFORMATION: Synthetically generated oligonucleotide
<221> NAME/KEY: CDS
<222> LOCATION: (3)...(95)
<221> NAME/KEY: CDS
<222> LOCATION: (99)...(116)

<400> SEQUENCE: 34

```
ta tac ata tgg cat ggc atg gcc act gca gga tcc acc acc atc atc         47
   Tyr Ile Trp His Gly Met Ala Thr Ala Gly Ser Thr Thr Ile Ile
   1               5                  10                 15 atc acg cat cac cac cac cac cat agg cca tca tca tca cca tca cac         95
Ile Thr His His His His His His Arg Pro Ser Ser Ser Pro Ser His
                20                  25                 30 tag ctg agt aag cat gcg acg tc                                          118
```

-continued

```
Leu Ser Lys His Ala Thr
              35

<210> SEQ ID NO 35
<211> LENGTH: 31
<212> TYPE: PRT
<213> ORGANISM: Artificial Sequence
<220> FEATURE:
<223> OTHER INFORMATION: Synthetically generated peptide

<400> SEQUENCE: 35

Tyr Ile Trp His Gly Met Ala Thr Ala Gly Ser Thr Thr Ile Ile Ile
 1               5                  10                  15

Thr His His His His His His Arg Pro Ser Ser Ser Pro Ser His
             20                  25                  30

<210> SEQ ID NO 36
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 36

Leu Ser Lys His Ala Thr
 1               5

<210> SEQ ID NO 37
<211> LENGTH: 118
<212> TYPE: DNA
<213> ORGANISM: Artificial Sequence
<220> FEATURE:
<223> OTHER INFORMATION: Synthetically generated oligonucleotide

<400> SEQUENCE: 37
gacgtcgcat gcttactcag ctagtgtgat ggtgatgatg atggcctatg gtggtggtgg      60
tgatgcgtga tgatgatggt ggtggatcct gcagtggcca tgccatgcca tatgtata      118
```